US010953209B2

(12) United States Patent
Story et al.

(10) Patent No.: US 10,953,209 B2
(45) Date of Patent: Mar. 23, 2021

(54) TREATING TUMORS USING TTFIELDS COMBINED WITH A PARP INHIBITOR

(71) Applicants: Michael Story, Dallas, TX (US); Debabrata Saha, Carrollton, TX (US); Narasimha Kumar Karanam, Dallas, TX (US)

(72) Inventors: Michael Story, Dallas, TX (US); Debabrata Saha, Carrollton, TX (US); Narasimha Kumar Karanam, Dallas, TX (US)

(73) Assignee: Board of Regents of the University of Texas System, Austin, TX (US)

(*) Notice: Subject to any disclaimer, the term of this patent is extended or adjusted under 35 U.S.C. 154(b) by 194 days.

(21) Appl. No.: 15/938,088

(22) Filed: Mar. 28, 2018

(65) Prior Publication Data

US 2019/0298982 A1    Oct. 3, 2019

(51) Int. Cl.
*A61M 37/00* (2006.01)
*A61P 35/00* (2006.01)
*A61K 31/502* (2006.01)
*A61N 5/10* (2006.01)

(52) U.S. Cl.
CPC ............ *A61M 37/00* (2013.01); *A61K 31/502* (2013.01); *A61N 5/10* (2013.01); *A61P 35/00* (2018.01); *A61M 2037/0007* (2013.01); *A61M 2205/051* (2013.01)

(58) Field of Classification Search
CPC . A61N 2005/1098; A61N 5/10; A61M 37/00; A61M 2205/051; A61M 2037/0007; A61K 31/502; A61P 35/00
See application file for complete search history.

(56) References Cited

U.S. PATENT DOCUMENTS

| 6,868,289 B2 | 3/2005 | Palti |
| 7,016,725 B2 | 3/2006 | Palti |
| 7,089,054 B2 | 8/2006 | Palti |

(Continued)

OTHER PUBLICATIONS

Kim EH, Kim YJ, Song HS, Jeong YK, Lee JY, Sung J, Yoo SH, Yoon M. Biological effect of an alternating electric field on cell proliferation and synergistic antimitotic effect in combination with ionizing radiation. Aug. 19, 2016. Oncotarget, vol. 7 No. 38, 62267-62279. (Year: 2016).*

(Continued)

*Primary Examiner* — Christine H Matthews
*Assistant Examiner* — Joshua Daryl D Lannu
(74) *Attorney, Agent, or Firm* — Potomac Law Group, PLLC

(57) ABSTRACT

Tumor-Treating Fields elicit a conditional vulnerability to PARP inhibitors (e.g., Olaparib) in certain cancer cells such as non-small cell lung cancer (NSCLC) cell lines. This conditional vulnerability is exploited in a method of killing cancer cells that comprises delivering a PARP inhibitor to the cancer cells and applying an alternating 80-300 kHz electric field to the cancer cells. At least a portion of the applying step is performed simultaneously with at least a portion of the delivering step. In some embodiments, an additional step of treating the cancer cells with a radiation therapy is added to the method. In some embodiments, the frequency of the alternating electric field is between 100 and 200 kHz.

23 Claims, 17 Drawing Sheets

(56) References Cited

U.S. PATENT DOCUMENTS

| | | | |
|---|---|---|---|
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 10,188,851 B2 | 1/2019 | Wenger et al. | |
| 2012/0035244 A1* | 2/2012 | Chinnaiyan | A61K 31/501 514/44 A |
| 2017/0093277 A1 | 3/2017 | Wasserman et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0001078 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |

OTHER PUBLICATIONS

Kirson ED, Schneiderman RS, Dbaly V, Tovarys F, Vymazal J, Itzhaki A, Mordechovich D, Gurvich Z, Shmueli E, Goldsher D, Wasserman Y, Palti Y. Chemotherapeutic treatment efficacy and sensitivity are increased by adjuvant alternating electric fields TRFields). BMC Medical Physics 2009, 9:1. (Year: 2009).*

Cavanagh et al., "The role of BRCA1 and BRACA2 mutations in prostate, pancreatic and stomach cancers," Hereditary Cancer in Clinical Practice, vol. 13, No. 16, 2015.

Cescutti et al., "TopBP1 functions with 53BP1 in the G1 DNA damage checkpoint," The EMBO Journal, vol. 29, pp. 3723-3732, 2010.

Chan et al., "Replication stress induces sister-chromatid bridging at fragile site loci in mitosis," Nature Cell Biology, vol. 11, No. 6, pp. 753-775, May 2009.

Das et al., "Non-Small Cell Lung Cancers with Kinase Domain Mutations in the Epidermal Growth Factor Receptor are Sensitive to Ionizing Radiation," Cancer Res., vol. 66, No. 19, pp. 9601-9608, Oct. 2006.

Davies et al., "Tumor treating fields: a new frontier in cancer therapy," Annals of the New York Academy of Sciences, vol. 1291, pp. 86-95, 2013.

Ding et al., "Enhanced identification and biological validation of differential gene expression via Illumina whole-genome expression arrays through the use of the model-based background correction methodology," Nucleic Acids Res., vol. 36, No. 10, p. e58, May 2008.

Foucquier et al., "Analysis of drug combinations: current methodological landscape," Pharmacology Research & Perspectives, vol. 3, Issue 3, p. e00149, 2015.

Geary et al., "Understanding synergy," Am. J. Physiol. Endocrinol. Metab., vol. 304, pp. E237-E253, Dec. 2012.

Gera et al., "Tumor Treating Fields Perturb the Localization of Septins and Cause Aberrant Mitotic Exit," Plos One, DOI:10.371, May 2015.

Giladi et al., "Alternating Electric Fields (Tumor-Treating Fields Therapy) Can Improve Chemotherapy Treatment Efficacy in Non-Small Cell Lung Cancer Both in Vitro and in Vivo," Seminars in Oncology, vol. 41, No. 5, Suppl. 6, pp. S35-S41, Oct. 2014.

Giladi et al., "Mitotic disruption and reduced clonogenicity of pancreatic cancer cells in vitro and in vivo by tumor treating fields," Pancreatology, vol. 14, pp. 54-63, 2014.

Giladi et al., "Mitotic Spindle Disruption by Alternating Electric Fields Leads to Improper Chromosome Segregation and Mitotic Catastrophe in Cancer Cells," Scientific Reports, vol. 5, No. 1, pp. 1-16, Dec. 2015.

Gonzalez et al., "Harnessing dielectric forces for separations of cells, fine particles and macromolecules," Journal of Chromatography A, vol. 1079, pp. 59-68, Apr. 2005.

Huyen et al., " Methylated lysine 79 of histone H3 targets 53BP1 to DNA double-strand breaks," Nature, vol. 432, pp. 406-411, Nov. 2004.

Inui et al., "Case Report: A Non-small Cell Lung Cancer Patient Treated with GcMAF, Sonodynamic Therapy and Tumor Treating Fields," Anticancer Research, vol. 36, pp. 3767-3770, 2016.

Kaelin, "The Concept of Synthetic Lethality in the Context of Anticancer Therapy," Nature Reviews Cancer, vol. 5, pp. 689-698, Sep. 2005.

Kan et al., "BRCA1 Mutation: A Predictive Marker for Radiation Therapy?," Int. J. Radiat. Oncol. Biol. Phys., vol. 93, No. 2, pp. 281-293, Oct. 2015.

Kim et al., "Bilogical effect of an alternating electric field on cell proliferation and synergistic antimitotic effect in combination with ionizing radiation," Oncotarget, vol. 7, No. 38, pp. 62267-62279, Aug. 2016.

Kirson et al, "Alternating electric fields (TTFields) inhibit metastatic spread of solid tumors to the lungs," Clin. Exp. Metastasis, vol. 26, pp. 633-640, Apr. 2009.

Kirson et al., "Alternating electric fields arrest cell proliferation in animal tumor models and human brain tumors," PNAS, vol. 104, No. 24, pp. 10152-10157, Jun. 2007.

Kirson et al., "Chemotherapeutic treatment efficacy and sensitivity are increased by adjuvant alternating electric fields (TTFields)," BMC Medical Physics, vol. 9, No. 1, Jan. 2009.

Kirson et al., "Disruption of Cancer Cell Replication by Alternating Electric Fields," Cancer Research, vol. 64, pp. 3288-3295, May 2004.

Lehar et al., "Chemical combination effects predict connectivity in biological systems," Molecular Systems Biology, vol. 3, No. 80, 2007.

McPherson et al., "A role for Brca1 in chromosome end maintenance," Human Molecular Genetics, vol. 15, No. 6, pp. 831-838, Jan. 2006.

Patel et al., "Involvement of Brca2 in DNA Repair," Molecular Cell, vol. 1, pp. 347-357, Feb. 1998.

Phillips et al., "Epidermal Growth Factor and Hypoxia-induced Expression of CXC Chemokine Receptor 4 on Non-small Cell Lung Cancer Cells is Regulated by the Phosphatidylinositol 3-Kinase/PTEN/AKT/Mammalian Target of Rapamycin Signaling Pathway and Activation of Hypoxia Inducible Factor 1-a," The Journal of Bilogical Chemistry, vol. 280, No. 23, pp. 22473-22481, Jun. 2005.

Roy et al., "BRCA1 and BRCA2: different roles in a common pathway of genome protection," Nat. Rev. Cancer, vol. 12, No. 1, pp. 68-78, Aug. 2016.

(56) References Cited

OTHER PUBLICATIONS

Schneiderman et al., "TTFields alone and in combination with chemotherapeutic agents effectively reduce the viablity of MDR cell sub-lines that over-express ABC transporters," BMC Cancer, vol. 10, No. 229, 2010.

Schultz et al., "p53 Binding Protein 1 (53BP1) is an Early Participant in the Cellular Response to DNA Double Strand Breaks," The Journal of Cell Biology, vol. 151, pp. 1381-13890, 2000.

Sichc et al., :"Telomeres and Telomerase in the Radiation Response: Implications for Instability, Reprograming, and Carcinogenesis,", Frontiers in Oncology, vol. 5, Article 257, Nov. 2015.

Sirbu et al., "Analysis of protein dynamics at active, stalled, and collapsed replication forks," Genes & Development, vol. 25, pp. 1320-1327, 2011.

Stupp et al., "Maintenance Therapy With Tumor-Treating Fields Plus Temozolomide vs. Temozolomide Alone for Glioblastoma—A Randomized Clinical Trial," JAMA, vol. 314, No. 23, pp. 2535-2543, Dec. 2015.

Su et al., "Replication stress induced site-specific phosphorylation targets WRN to the ubiquitin-proteasome pathway," Oncotarget, vol. 7, No. 1, pp. 46-65, Dec. 2015.

Turner et al., "Hallmarks of 'BRCAness' in sporadic cancers," Nature Reviews, vol. 4, pp. 1-6, Oct. 2004.

Venere et al., "Phosphorylation of ATR-Interacting Protein on Ser239 Mediates and Interaction with Breast-Ovarian Cancer Susceptibility 1 and Checkpoint Function," Cancer Res., vol. 67, No. 13, pp. 6100-6105, Jul. 2007.

Voloshin et al., "Alternating electric fields (TTFields) in combination with paclitaxel are therapeutically effective against ovarian cancer cells in vitro and in vivo," International Journal of Cancer, vol. 139, pp. 2850-2858, 2016.

Vymazal et al., "Response Patterns of Recurrent Glioblastomas Treated with Tumor-Treating Fields," Seminars in Oncology, vol. 41, No. 5, pp. S14-S24, Oct. 2014.

Wong et al., "Response assessment of NovoTTF-100A versus best physician's choice chemotherapy in recurrent glioblastoma," Cancer Medicine, vol. 3, No. 3, pp. 592-602, 2014.

\* cited by examiner

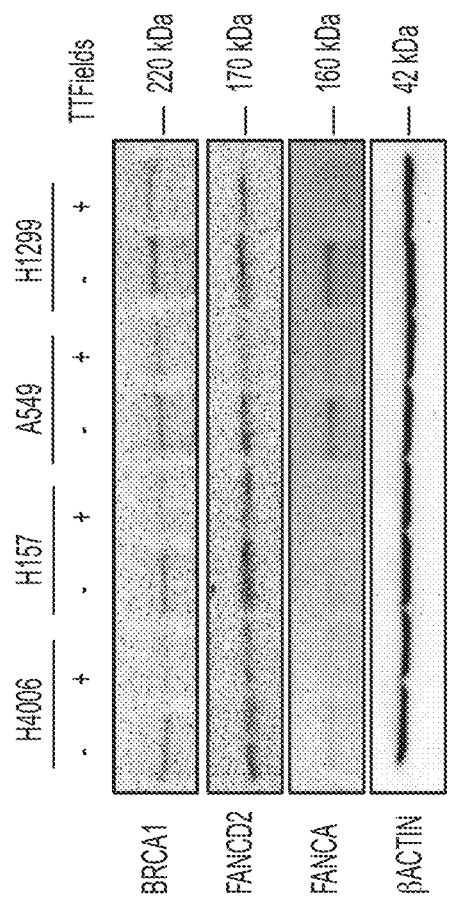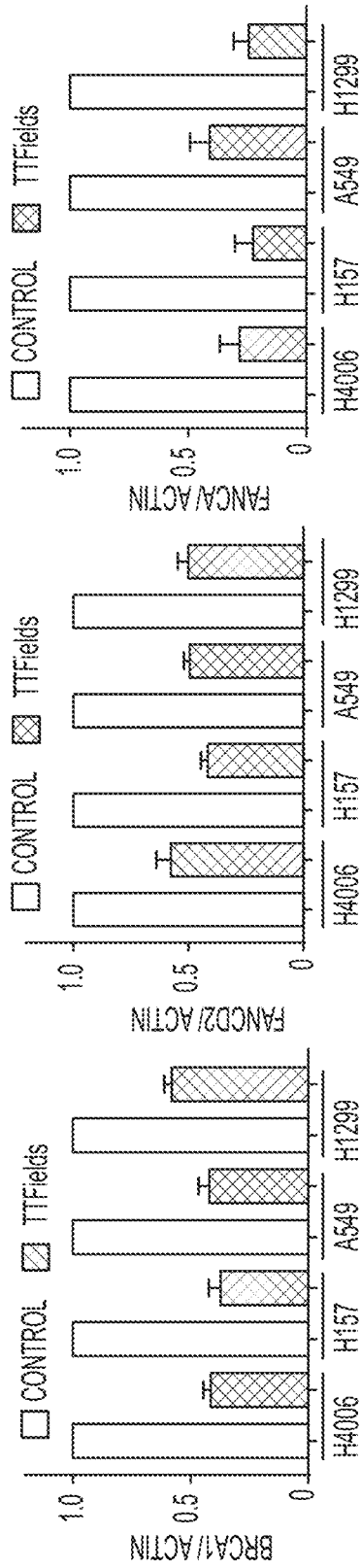
FIG. 3B
FIG. 3A
FIG. 4

TREATING TUMORS USING TTFIELDS COMBINED WITH A PARP INHIBITOR

BACKGROUND

Lung cancer is the second most prevalent cancer and the leading cause of cancer-related death in the United States. Non-small cell lung cancer (NSCLC) is the most prevalent type, accounting for ~80% of new cases. A plethora of treatment options exist including surgical resection, chemotherapy, radiation therapy, and immunotherapy. Five-year survival rates for patients with stage I and II NSCLC are ~50% and 30%, respectively. However, despite this myriad of options, 5-year survival rates for patients with late stage IIIA, IIIB and IV are 14%, 5% and 1%, respectively, highlighting the need for novel treatment modalities that can be utilized alone or in combination with conventional therapies to increase survival rates.

The advent of Tumor-Treating Fields (TTFields), a novel physical treatment modality, has been effective for the treatment of solid, therapy-resistant primary and recurrent tumors. TTFields electrodes are non-invasive and deliver a low-intensity (e.g., 1-3 V/cm) intermediate frequency (e.g., 100-300 kHz) alternating electric field across the tumor bed. TTFields create a heterogeneous intracellular environment that induces a dielectrophoretic movement of polar molecules toward the region of higher field intensity, effectively preventing polymerization and other critical biochemical functions. As such, TTFields preferentially target cancer cells through the exploitation of cell proliferation, effectively sparing non-dividing normal cells. In addition, TTFields do not stimulate nerves and muscle because of their high frequency, and do not generate high levels of heating because of their low intensity. The FDA has approved Optune (NovoCure), a TTFields generating transducer array, for the treatment of recurrent and newly diagnosed glioblastoma (GBM) in combination with temozolomide.

SUMMARY OF THE INVENTION

One aspect of the invention is directed to a first method of killing cancer cells. The first method comprises delivering a PARP inhibitor to the cancer cells; and applying an alternating electric field to the cancer cells. The alternating electric field has a frequency between 80 and 300 kHz, and at least a portion of the applying step is performed simultaneously with at least a portion of the delivering step.

In some embodiments of the first method, the PARP inhibitor comprises Olaparib. In some embodiments of the first method, the cancer cells are NSCLC cells. In some embodiments of the first method, the applying step has a duration of at least 72 hours. In some embodiments of the first method, the frequency of the alternating electric field is between 100 and 200 kHz.

In some embodiments of the first method, the PARP inhibitor is delivered to the cancer cells at a therapeutically effective concentration, and the alternating electric field has a field strength of at least 1 V/cm in at least some of the cancer cells. In some of these embodiments, the applying step has a duration of at least 72 hours and the frequency of the alternating electric field is between 100 and 200 kHz. In some of these embodiments, the PARP inhibitor comprises Olaparib. In some of these embodiments, the cancer cells are NSCLC cells.

Another aspect of the invention is directed to a second method of killing cancer cells. The second method comprises delivering a PARP inhibitor to the cancer cells; applying an alternating electric field to the cancer cells; and treating the cancer cells with a radiation therapy. The alternating electric field has a frequency between 80 and 300 kHz, and at least a portion of the applying step is performed simultaneously with at least a portion of the delivering step.

In some embodiments of the second method, the PARP inhibitor comprises Olaparib. In some embodiments of the second method, the cancer cells are NSCLC cells. In some embodiments of the second method, the PARP inhibitor is delivered to the cancer cells at a therapeutically effective concentration, and the alternating electric field has a field strength of at least 1 V/cm in at least some of the cancer cells.

In some embodiments of the second method, the PARP inhibitor is delivered to the cancer cells at a therapeutically effective concentration, and the alternating electric field has a field strength of at least 1 V/cm in at least some of the cancer cells, and the delivering, applying, and treating steps are repeated at least five times. In some of these embodiments, each repetition of the treating step comprises delivering at least 2 Gy of radiation to a target area. In some of these embodiments, each repetition of the treating step comprises delivering at least 4 Gy of radiation to a target area. In some of these embodiments, the frequency of the alternating electric field is between 100 and 200 kHz. In some of these embodiments, the treating step is performed immediately after the applying step in each repetition. In some of these embodiments, the applying step is performed immediately after the treating step in each repetition.

BRIEF DESCRIPTION OF THE DRAWINGS

FIG. 3A shows z-scores and P-values of BRCA1 pathway gene expression along with the relevant pathway gene names.

FIG. 3B depicts immunoblots of representative BRCA1 pathway genes resulting from TTFields treatment.

FIG. 4 depicts a quantification of immunoblots indicating that certain protein levels were downregulated after exposure to TTFields.

Figure 1:
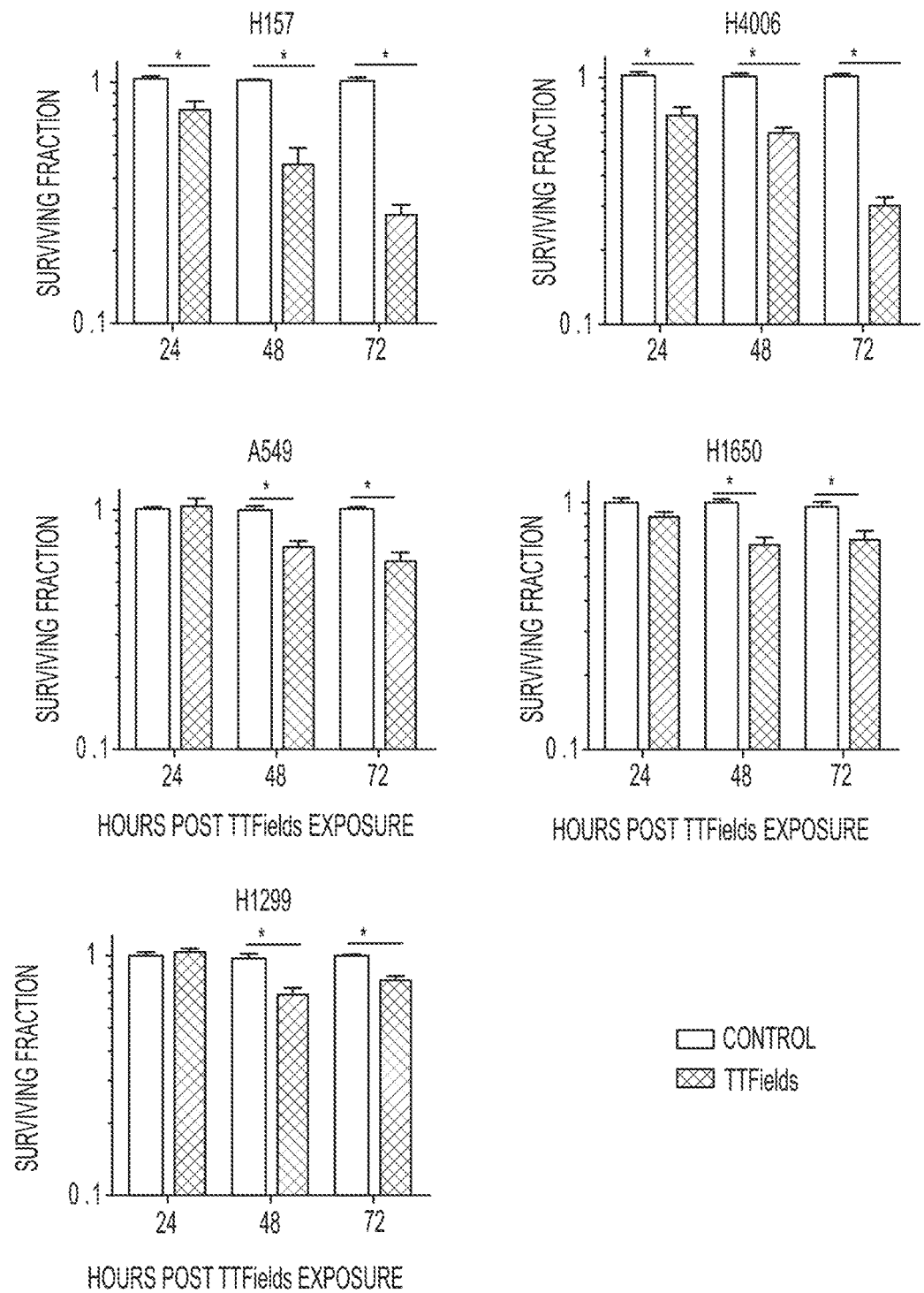
FIG. 1 shows the fraction of cells surviving TTFields treatment for different NSCLC cell lines.
Figure 2A:
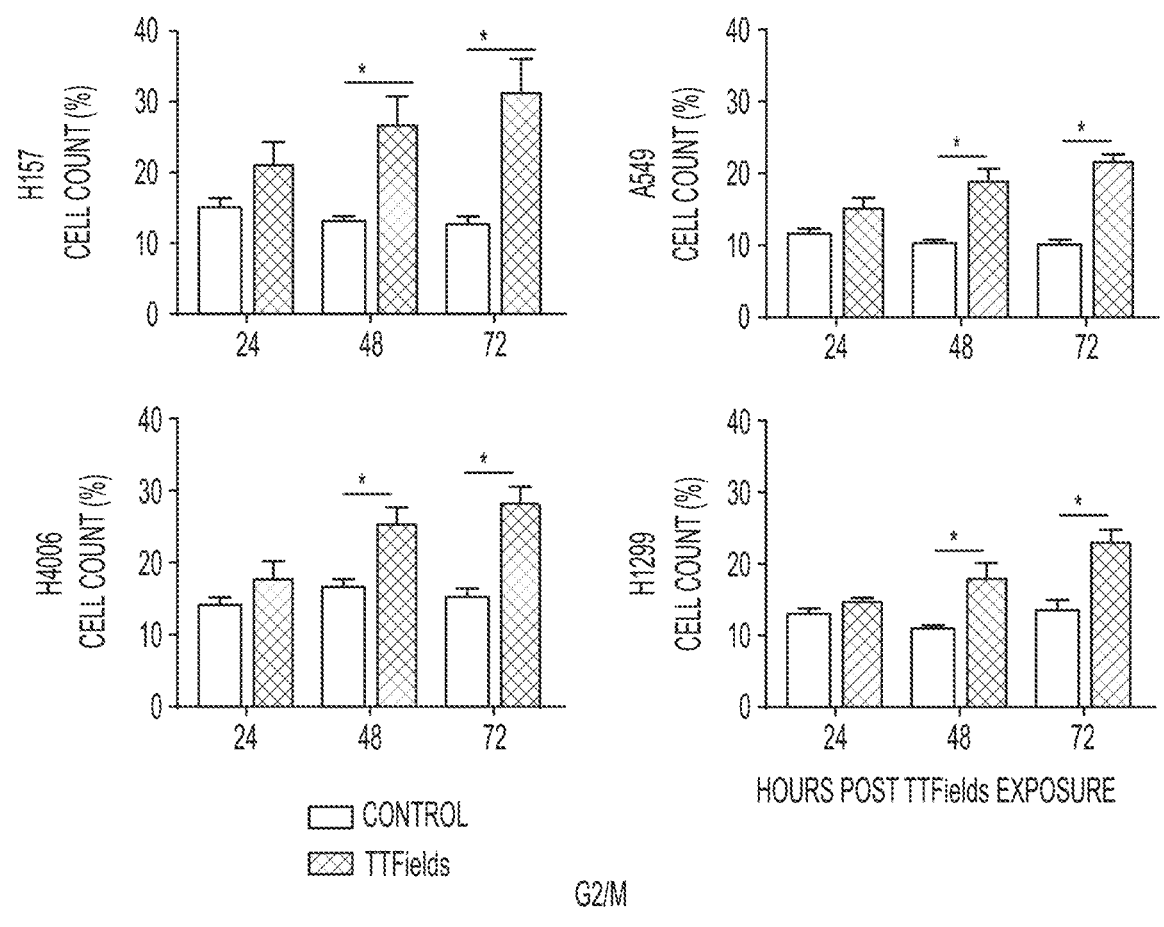
FIGS. 2A-D show the impact of TTFields treatment on NSCLC cells in the G2/M phase, the S-phase, the sub-G1 phase, and the G1 phase, respectively.
Figure 2B:
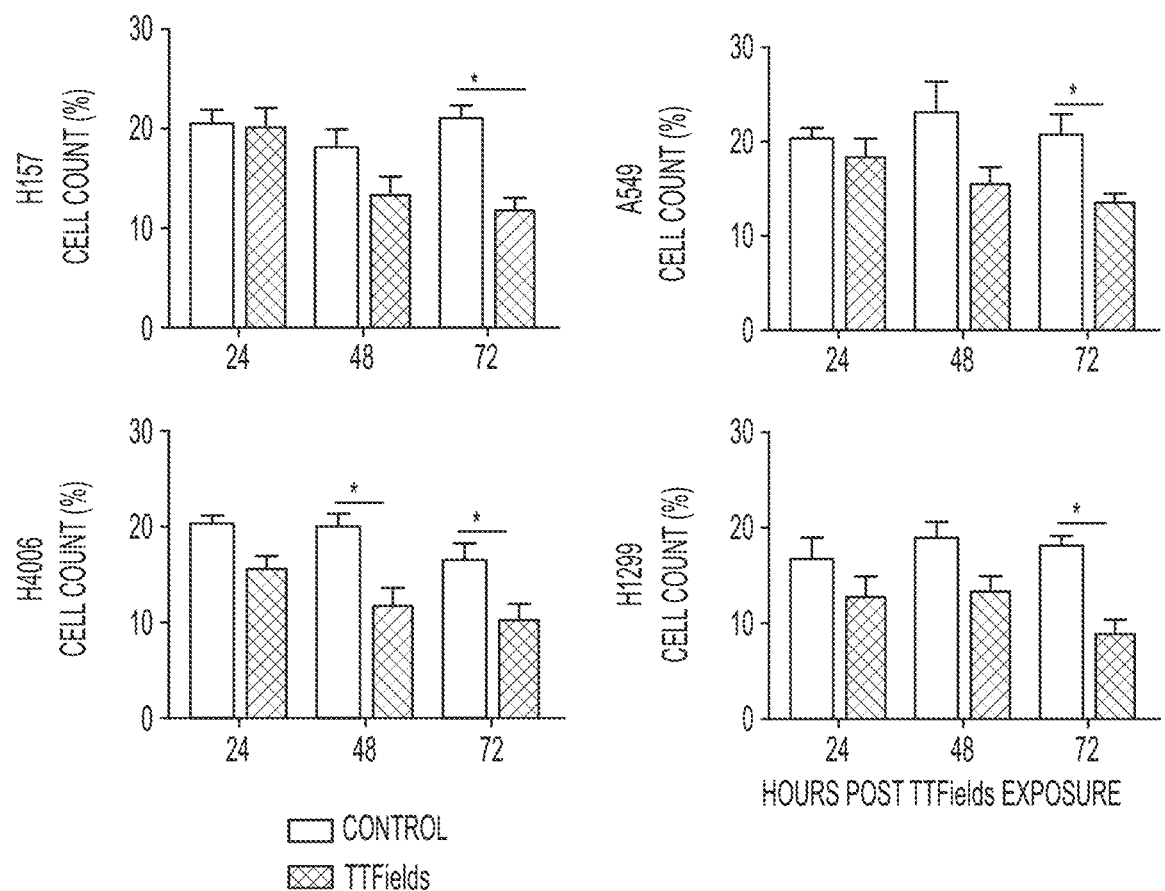
Figure 2C:
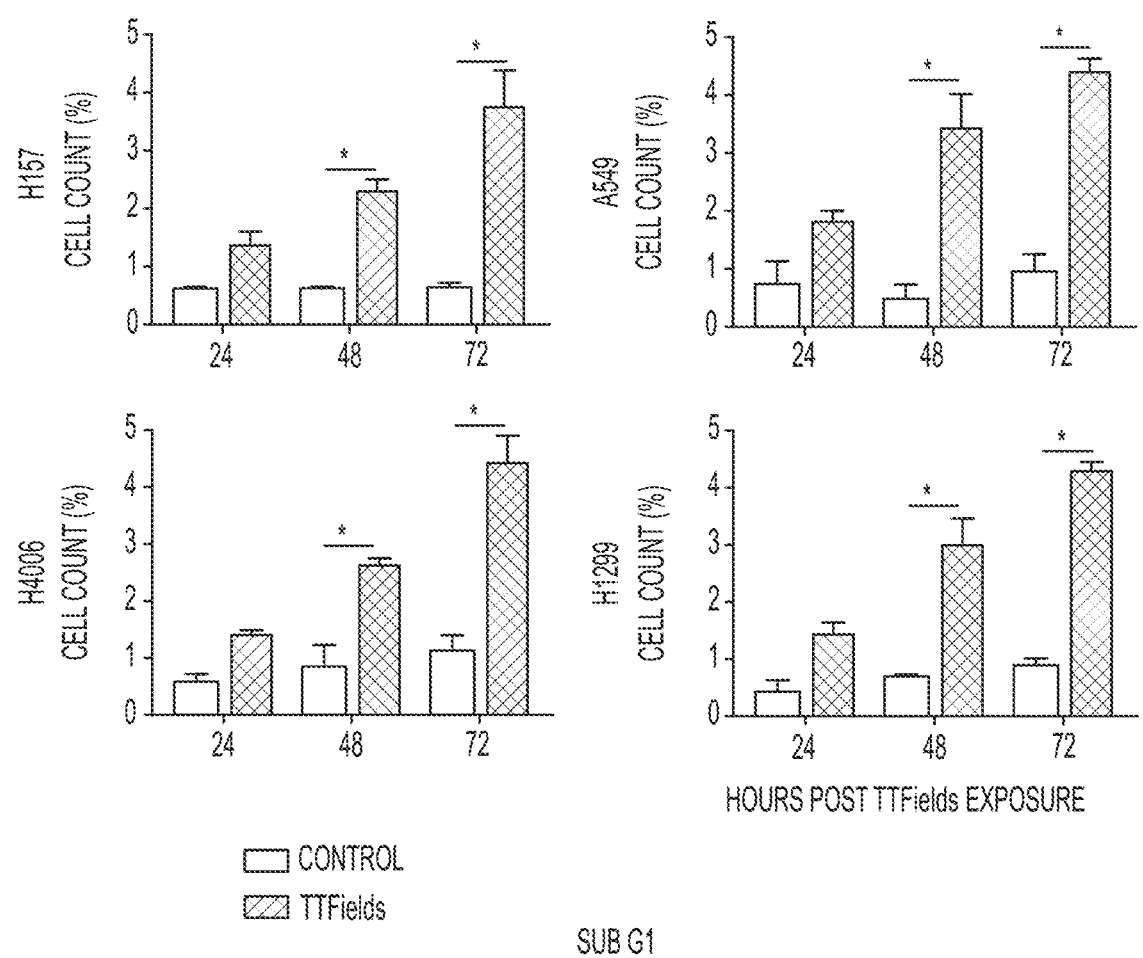
Figure 2D:
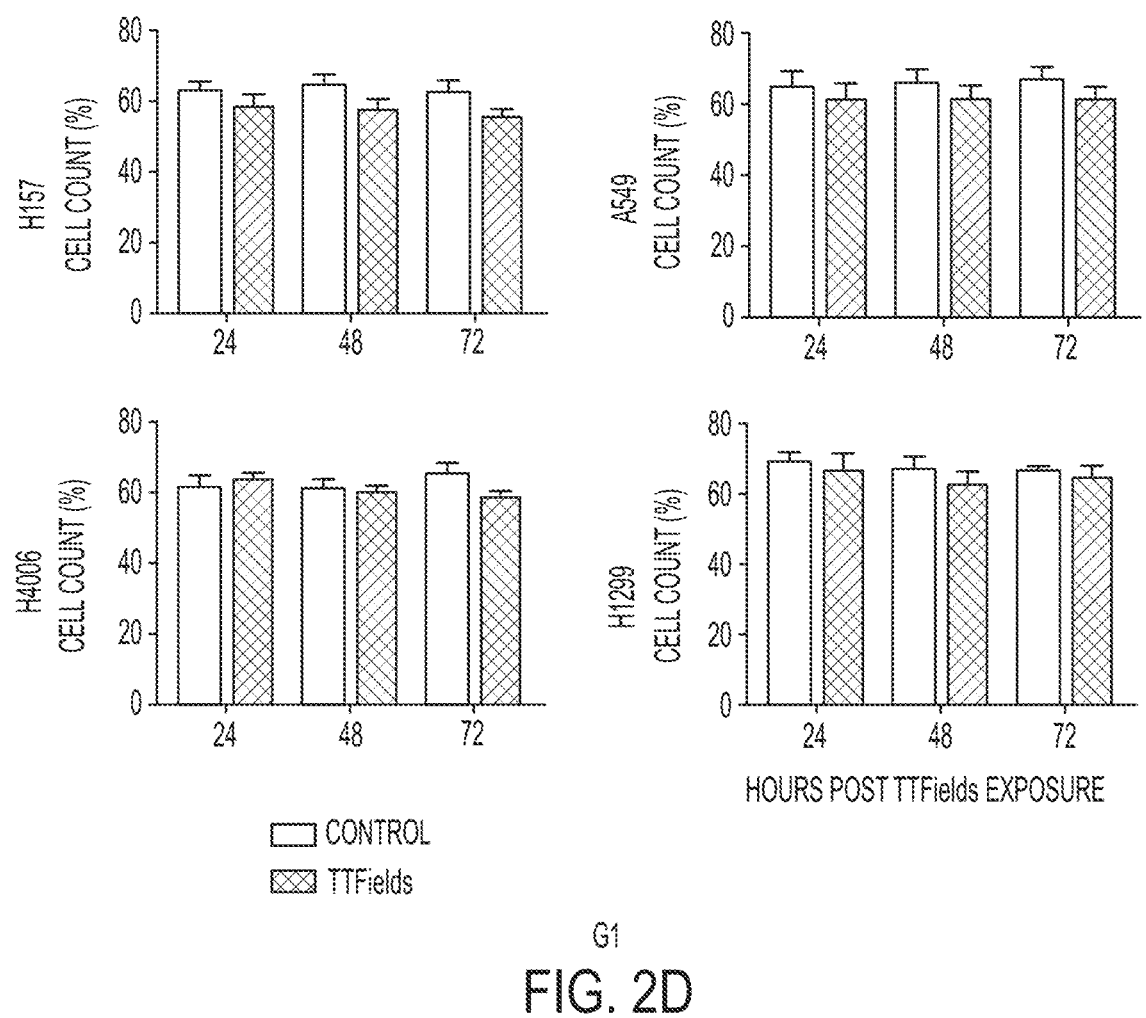

Various embodiments are described in detail below with reference to the accompanying drawings.

DESCRIPTION OF THE PREFERRED EMBODIMENTS

Tumor-Treating Fields Elicit a Conditional Vulnerability to Ionizing Radiation (IR) and PARP Inhibitors Via the Downregulation of BRCA1 Signaling and Reduced DNA Double-Strand Break Repair Capacity in Non-Small Cell Lung Cancer Cell Lines: The use of tumor-treating fields (TTFields) has revolutionized the treatment of recurrent and newly diagnosed glioblastoma (GBM). TTFields are low-intensity, intermediate frequency, alternating electric fields that are applied to tumor regions and cells using non-invasive arrays. The predominant mechanism by which TTFields are thought to kill tumor cells is the disruption of mitosis. Using five non-small cell lung cancer (NSCLC) cell lines, the inventors found that there is a variable response in cell proliferation and cell killing between these NSCLC cell lines that was independent of p53 status. TTFields treatment increased the G2/M population, with a concomitant reduction in S-phase cells followed by the appearance of a sub-G1 population indicative of apoptosis. Temporal changes in gene expression during TTFields exposure was evaluated to identify molecular signaling changes underlying the differential TTFields response. The most differentially expressed genes were associated with the cell cycle and cell proliferation pathways. However, the expression of genes found within the BRCA1 DNA-damage response were significantly downregulated (P<0.05) during TTFields treatment. DNA double-strand break (DSB) repair foci increased when cells were exposed to TTFields as did the appearance of chromatid-type aberrations, suggesting an interphase mechanism responsible for cell death involving DNA repair. Exposing cells to TTFields immediately following ionizing radiation resulted in increased chromatid aberrations and a reduced capacity to repair DNA DSBs, which may be responsible for at least a portion of the enhanced cell killing seen with the combination. These findings suggest that TTFields induce a state of 'BRCAness' leading to a conditional susceptibility resulting in enhanced sensitivity to ionizing radiation and supports the use of TTFields as a combined modality therapy with radiation, PARP inhibitors, or other DNA-damaging agents.

TTFields are known to decrease cellular proliferation and induce abortive apoptosis in dividing cancer cells across a variety of human and rodent tumor cell lines. Prevention of proper formation of the mitotic spindle apparatus and the activation of the mitotic spindle checkpoint has been proposed as the mechanism by which TTFields kill dividing cells. Specifically, TTFields exposure leads to microtubule depolymerization and the mislocalization of septin. This results in plasma membrane instability and blebbing that disrupts cytokinesis, leading to abnormal chromosome segregation, aberrant mitotic exit and production of deranged cells that subsequently undergo apoptosis.

In the context of cancer therapy, TTFields has been shown to enhance the efficacy of numerous chemotherapeutic agents when used in combination such as paclitaxel and doxorubicin in multidrug-resistant cancer cells—without increasing the intracellular accumulation of the drugs; decreased cellular proliferation, survival and the percentage of G2/M populations; enhanced the efficacy of chemotherapy in a hamster pancreatic cancer model; decreased cellular proliferation and enhanced the efficacy of pemetrexed, cisplatin and paclitaxel in NSCLC cells both in vitro and in vivo. In addition to its efficacy in treating primary tumors, TTFields have also demonstrated the ability to prevent or delay metastasis in animal models, a process that may result from enhancement of the antitumor immune response. Furthermore, TTFields apparently enhance the efficacy of radiation treatment through the induction of increased mitotic abnormalities and induction of DNA damage in GBM. Although these findings collectively support the efficacy of TTFields as an anticancer agent, further mechanistic insights are needed to optimize the use of TTFields in combination with additional modalities including radiation therapy and PARP inhibitors.

Using a panel of NSCLC cell lines with different molecular phenotypes, the inventors found that TTFields alone exhibit antiproliferative effects and cytotoxicity. The inventors divided NSCLC cells into more responsive (H157 and H4006) and less responsive (A549, H129, H1650) cell lines based on their degree of responsiveness to TTFields. Consistent with previous reports, the inventors also observed a time-dependent increase in the G2/M population upon TTFields exposure; however, the number of cells accumulating in G2/M was likely not enough to account for the decreased survival seen.

The inventors postulated that TTFields may induce additional mechanisms leading to cell death. To explore this phenomenon and identify novel mechanisms that could be exploited clinically, the inventors performed temporal gene expression analysis after treating H157, H4006, A549, H1650 and H1299 cell lines with TTFields for up to 48 h. In addition to confirming previously described mechanisms with the perturbation of genes involved in cell cycle regulation and mitosis, the inventors also identified a significant association of differentially expressed genes to the BRCA1 pathway (P<0.05) upon TTFields treatment. This finding suggests that a novel mechanism involving DNA repair and/or DNA replication may contribute to TTFields induced cell killing other than the reported abortive mitosis cell death mechanism. TTFields alone elevated the frequency of chromatid-type aberrations and induced $\gamma$-H2AX foci, in addition to slowing the repair of ionizing radiation (IR)-induced double-strand breaks (DSBs).

The inventors recognized that TTFields sensitized NSCLC cells to IR and decreased the surviving fraction at 2 and 4 Gy. The effect was at least additive and, in some cases, synergistic. Taken together, these results highlight a previously unknown mechanism for TTFields-induced cell killing, and also suggest that TTFields may establish a 'conditional vulnerability' resulting from an induced state of 'BRCAness' effectively sensitizing cells to IR and opening new avenues for combination therapy with DNA-damaging agents and other agents such as PARP inhibitors.

Results

TTFields Reduce NSCLC Cell Proliferation:

Previous studies have demonstrated that TTFields exhibit optimal effectiveness in a cell line-specific manner. To determine the optimal frequency to maximize growth inhibition, cells were treated at different frequencies ranging from 100 to 300 kHz. Cell counts were taken every 24 h for up to 72 h within a panel of NSCLC cell lines. Table 1 lists the NSCLC cell lines utilized in this study, and for each of those cell lines: their standardized optimized frequency at which maximal growth inhibition was observed, average percentage of growth inhibition at the optimized frequency after 72 h of TTFields exposure, genetic background information (i.e., their p53 and KRAS mutation status), and the cell cycle-doubling time (N=3). Further experimentation was carried out at the optimal frequencies listed in Table 1. As reflected in Table 1, while TTFields reduced the growth in all the cell lines examined, its relative efficacy was lower in the H1650, H1299, and A549 cell lines and higher in the H157 and H4006 cell lines.

TABLE 1

| Cell line | Standardized TTFields frequency (kHz) | % of growth inhibition at 72 h | P53 status | KRAS status | Doubling time (h) |
|---|---|---|---|---|---|
| H157 | 100 | 72 | Mutant | Wild type | 36 |
| H4006 | 150 | 69 | SNP MS | Wild type | 34 |
| A549 | 200 | 48 | Wild type | Mutant | 22 |
| H1299 | 100 | 32 | Mutant | Wild type | 20 |
| H1650 | 100 | 21 | Wild type | Wild type | 26 |

TTFields Exposure Causes Cell Death in NSCLC Cell Lines:

As growth delay is not the same as cell killing, the inventors examined the ability of TTFields to induce reproductive cell death using clonogenic survival assays. TTFields treatment resulted in a significant decrease in cell survival in all the cell lines examined, a trend that generally increased with the amount of time cells were exposed to TTFields. More specifically, FIG. 1 shows the fraction of cells surviving TTFields treatment at 24, 48 and 72 h post induction in a panel of NSCLC cell lines including H157, H1299, A549, H1650, and H4006. Values are represented as the number of colony-forming cells relative to control. Error bars represent the S.E.M. of three separate experiments and asterisks represent values where survival was significantly (P<0.05) decreased. As with the cell growth patterns, H1650, H1299, and A549 were less responsive and H157 and H4006 more responsive, to TTFields. The characterization of more responsive versus less responsive was maintained for all assays in this study.

TTFields Exposure Alters the Cell Cycle Distribution by Enriching the G2/M Population and Generating a Sub-G1 Population:

Previous reports have established that TTFields alter the cell cycle distribution, resulting in an increase in the G2/M phase of the cell cycle with increasing treatment time in GBM and ovarian cancer cell lines. The inventors set out to determine whether TTFields induce a similar enrichment of the G2/M population in NSCLC cell lines. To do this, the inventors performed propidium iodide (PI) staining and examined the distribution of cells throughout the cell cycle using flow cytometry in the two most responsive cell lines (H157 and H4006) and two of the less responsive cell lines (A549 and H1299).

The inventors' experiments revealed that TTFields treatment enriched the G2/M and G0/G1 populations while decreasing the number of S-phase cells in all cell lines tested. More specifically, FIGS. 2A-D shows that TTFields treatment resulted in a significant enrichment of NSCLC cells in the G2/M phase of the cell cycle (FIG. 2A), a decrease in the percentage of cells in S-phase (FIG. 2B), and resulted in the significant induction of a sub-G1 population (FIG. 2C) indicative of an apoptotic cell population. The percentage of cells in the G1 phase is provided in FIG. 2D for completeness. Error bars represent the S.E.M. of three separate experiments and asterisks represent significant changes (P<0.05) in cell count percentage at a given time point and for a given cell line.

That TTFields generated a sub-G1 population gives strong, albeit not definitive, evidence for an apoptotic cell population. These changes in cell cycle distribution are likely not sufficient to account for the amount of cell death observed with TTFields application. The inventors postulated that additional mechanism(s), aside from cell cycle perturbation and abortive apoptosis following mitosis, must be contributing to TTFields-induced cell death.

TTFields Induce Global Gene Expression Changes:

To explore alternative potential mechanisms for TTFields-induced cell death, the inventors performed gene expression analysis on a panel of NSCLC cells exposed to TTFields for up to 48 h. Differential gene expression after TTFields exposure was examined using significance analysis of microarray (SAM) time course analysis. By normalizing TTFields-induced gene expression to the baseline gene expression values for each cell line, the inventors identified a 1083 gene (false discovery rate (FDR)<0.01) signature that segregates cell lines by response to TTFields exposure. Gene expression analysis was subsequently performed in more responsive and less responsive cell groups, respectively. The analysis suggested that, as a result of TTFields exposure, the expression of 1039 genes was altered in the less responsive cell lines and that 628 genes were differentially expressed in the more responsive NSCLC cell lines. More specifically, data depicting supervised clustering using a 1083 gene (FDR<0.01) signature that segregates cell lines by response to TTFields exposure was obtained. Clustering analysis of differentially expressed genes after TTFields treatment revealed that 628 genes (FDR<0.05) responded to TTFields in the more responsive cell lines, and 1039 genes (FDR<0.05) responded to TTFields in the less responsive cell lines. Cluster analysis showed distinct expression profiles that separated the 48 h time point from earlier time points relative to untreated controls in the more responsive lines as well as in less responsive cell lines.

Ingenuity pathway analysis (IPA) was performed to determine specific canonical pathways involved in the TTFields responding genes. This analysis identified differentially regulated canonical pathways for TTFields exposure in the more responsive and the less responsive cell lines. Downregulation of the BRCA1 DNA damage repair pathway was more pronounced in the more responsive cell lines compared to the less responsive cell lines, which was associated with negative z-scores. The results suggested that alterations occurred in cell cycle and mitotic regulatory pathways, which is consistent with previous studies, but also revealed a significantly downregulated BRCA1 DNA-damage response pathway (P<0.05) with TTFields exposure.

BRCA1 Pathway Genes are Downregulated as a Result of TTFields Treatment:

Based on IPA analysis of differentially expressed genes, the inventors theorized that the activity of the BRCA1 pathway was inhibited in NSCLC cells as a result of TTFields exposure. Although inhibition occurred in both groups, the inventors observed a stronger inhibition in the more responsive cell lines compared to the less responsive cell lines as indicated by the negative z-scores. This is depicted in FIG. 3A, which shows z-scores and P-values of BRCA1 pathway gene expression along with the relevant pathway gene names.

Temporal gene expression graphs revealed downregulation of many of the BRCA1 pathway genes in all cell lines. The confirmation of BRCA1 pathway gene downregulation at the protein level was conducted with immunoblotting for BRCA1, FANCD2 and FANCA, and FIG. 3B depicts immunoblots of representative BRCA1 pathway genes demonstrating the downregulation of BRCA1, FANCD2, and FANCA protein levels resulting from TTFields treatment at 72 h. FIG. 4 depicts the quantification of immunoblots (N=3), which reveals that BRCA1, FANCD2, and FANCA protein levels were significantly downregulated in all cell lines at 72 h post-TTFields exposure, confirming gene expression results.

Figure 5A:
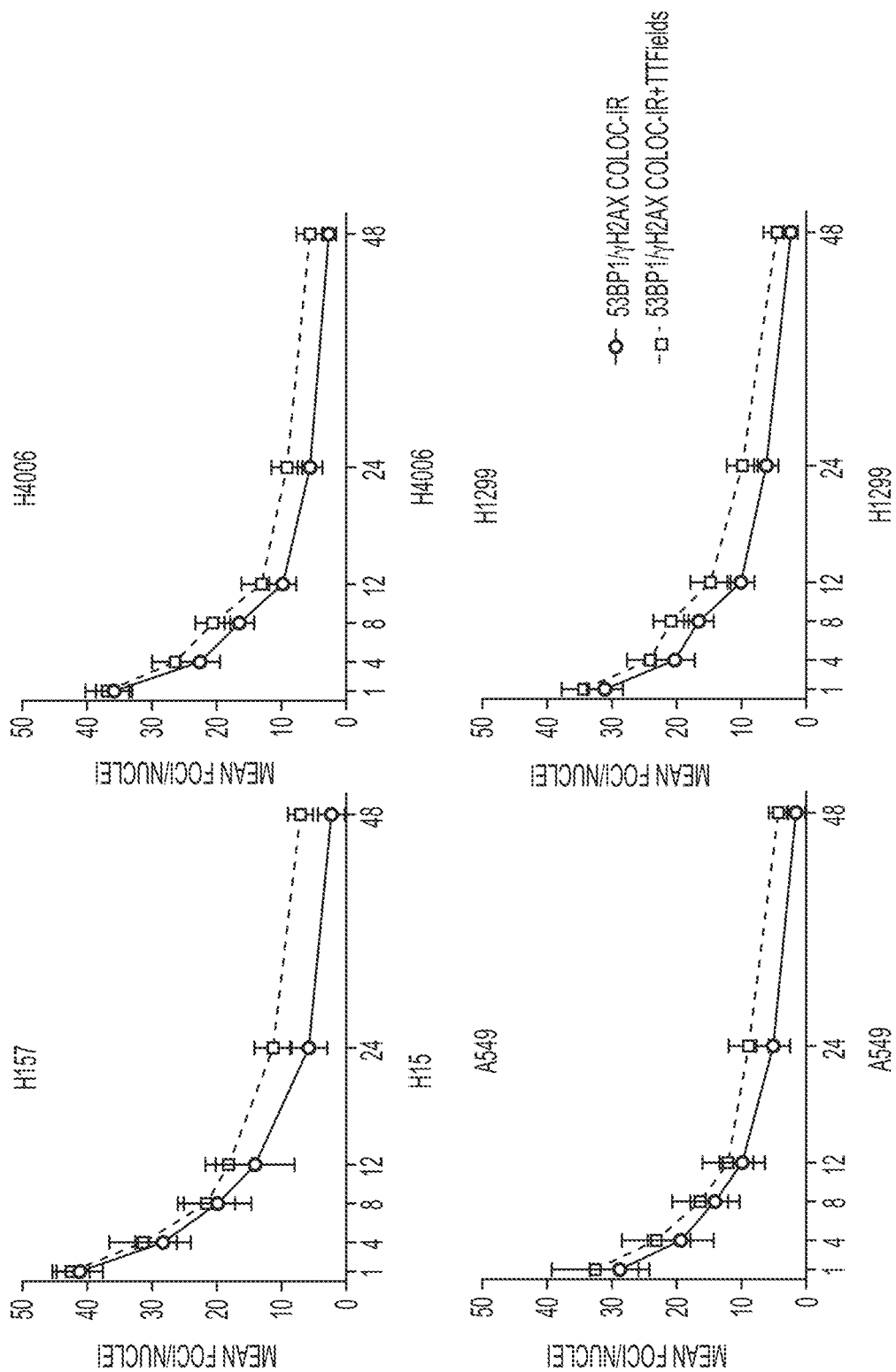
FIG. 5A shows how exposure to TTFields changes the mean number of localized 53BP1 and γ-H2AX foci for different cell lines.
Figure 5B:
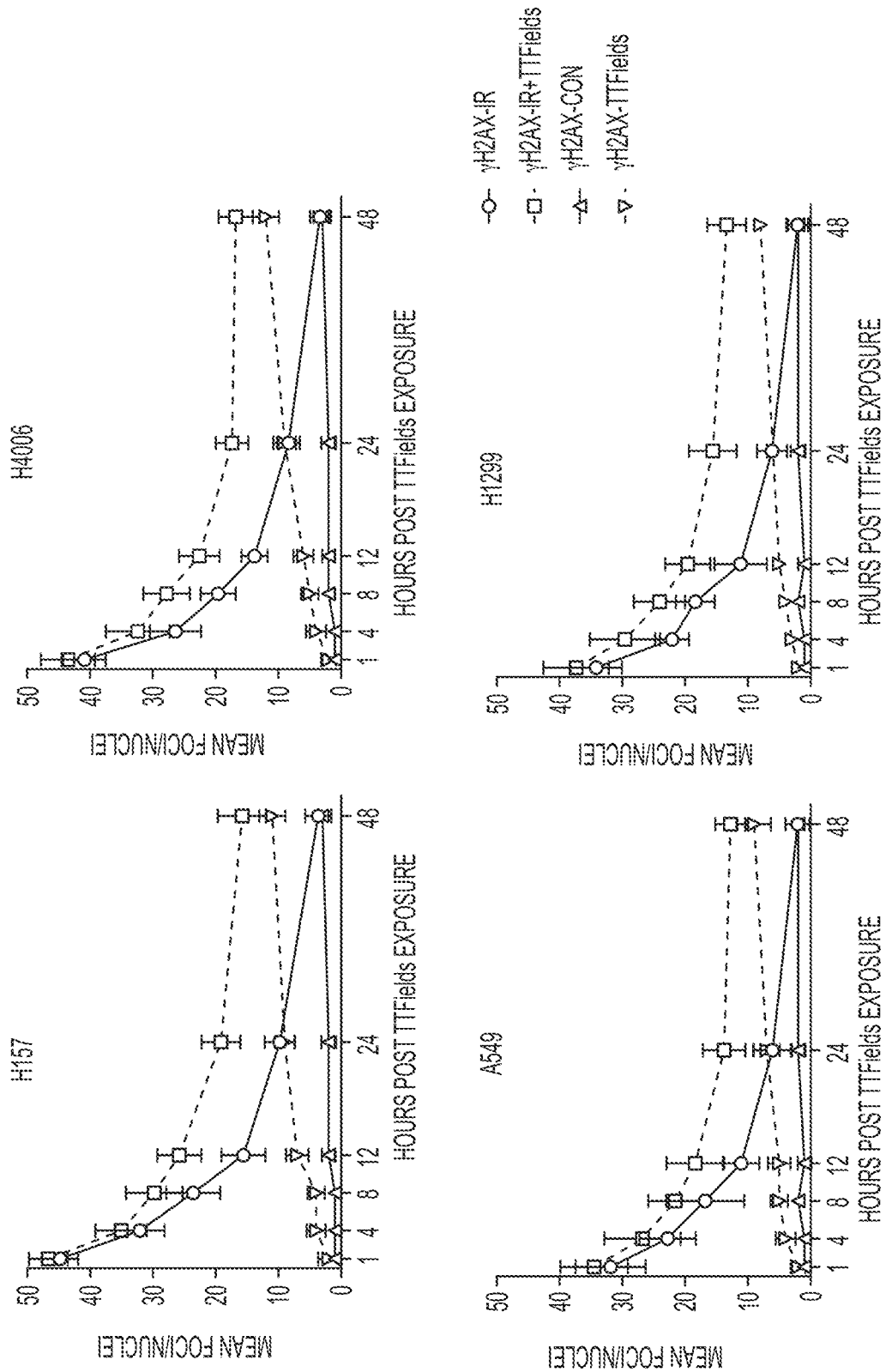
FIG. 5B shows the change in the mean number of γ-H2AX foci over time with TTFields and 2 Gy of radiation for different cell lines.

TTFields Cause DNA Damage, Reduce IR-Induced DNA Repair, and Increase the Frequency of Chromatid-Type Aberrations:

Because TTFields decreased BRCA1-associated gene expression, the inventors wanted to confirm whether this resulted in DNA damage induction as a result of TTFields exposure alone or whether there would be a reduction in DNA DSB repair kinetics after IR. Exposure to TTFields alone resulted in the formation of $\gamma$-H2AX foci, with the mean number of foci per cell increasing as a function of time, indicating to the inventors that TTFields treatment alone is capable of causing DNA damage. These findings are depicted in FIG. 5B, which shows the change in the mean number of $\gamma$-H2AX foci over time with TTFields alone (triangle icons) and after receiving 2 Gy (round and square icons), both followed for four different cell lines over 48 h; and in FIG. 5C, which shows the mean value for residual $\gamma$-H2AX foci and localized 53BP1 and $\gamma$-H2AX foci at 48 h post-IR for all four cell lines after TTFields exposure in combination with radiation.

An IR exposure of 2 Gy immediately followed by TTFields application decreased the resolution of $\gamma$-H2AX foci and colocalized $\gamma$-H2AX/53BP1 foci, indicating to the inventors that in addition to causing DNA damage TTFields also reduced the repair of IR-induced damage. These findings are depicted in FIG. 5A, which shows the changes in the mean number of localized 53BP1 and $\gamma$-H2AX foci for four different cell lines over 48 h of exposure to TTFields; as well as in FIG. 5B. When residual lesions at 24 and 48 h were compared, the more responsive cell lines had greater numbers of residual lesions compared to those cell lines considered as less responsive.

Figure 5C:
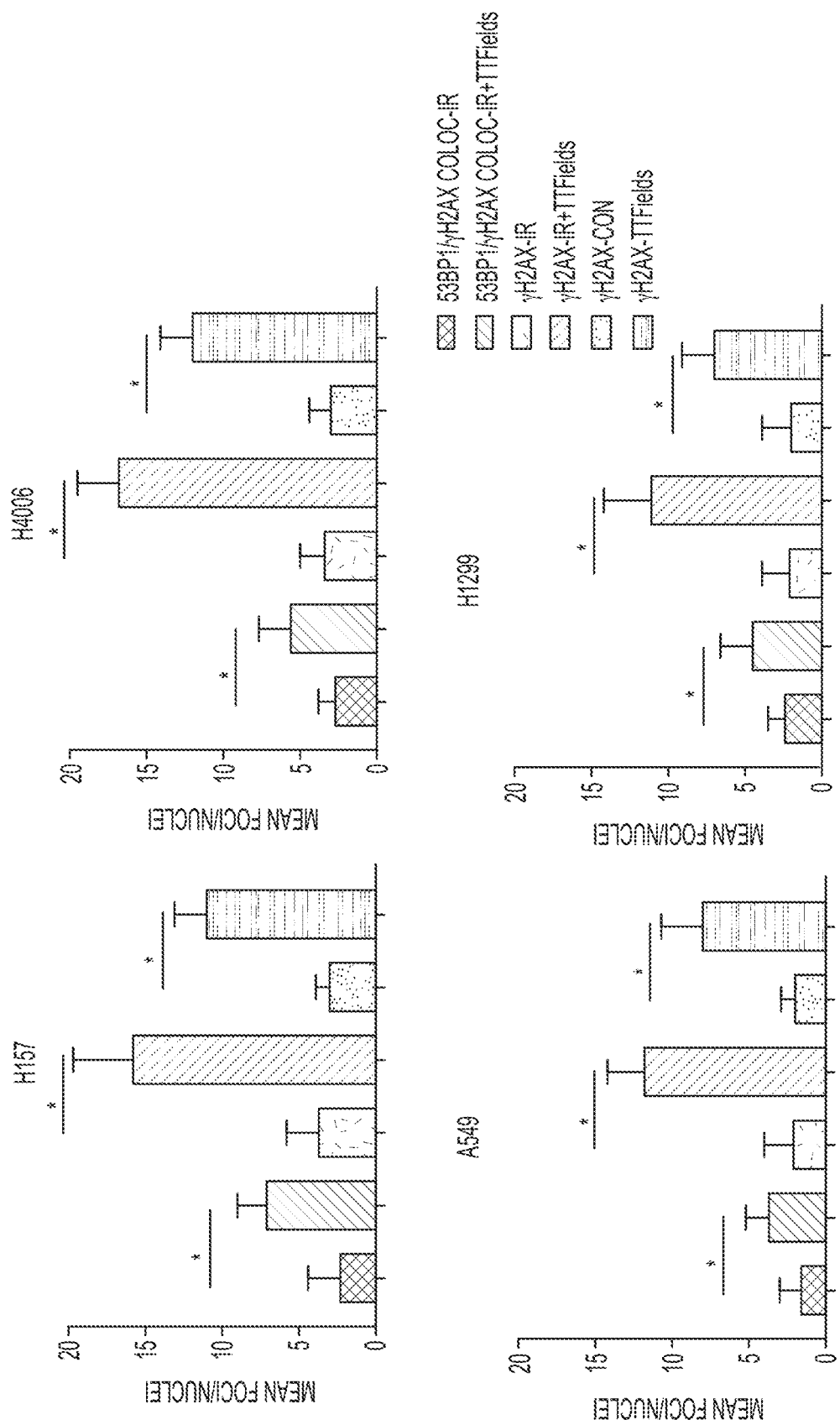
FIG. 5C shows the mean value for residual γ-H2AX foci and localized 53BP1 and γ-H2AX foci for different cell lines after TTFields exposure in combination with radiation.
Figure 5D:
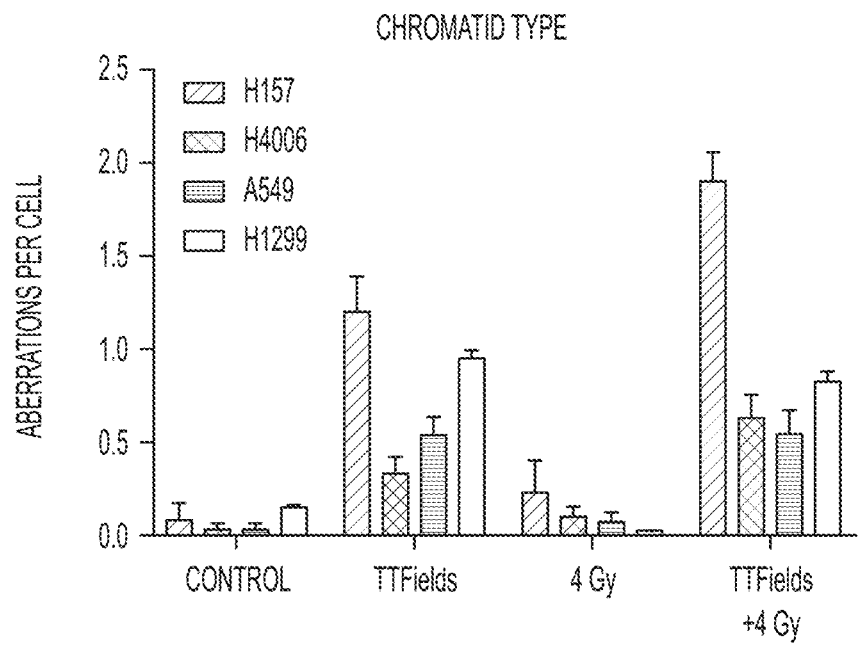
FIG. 5D shows the induction of chromatid-type aberrations in different NSCLC lines after TTFields exposure in combination with radiation.
Figure 5E:
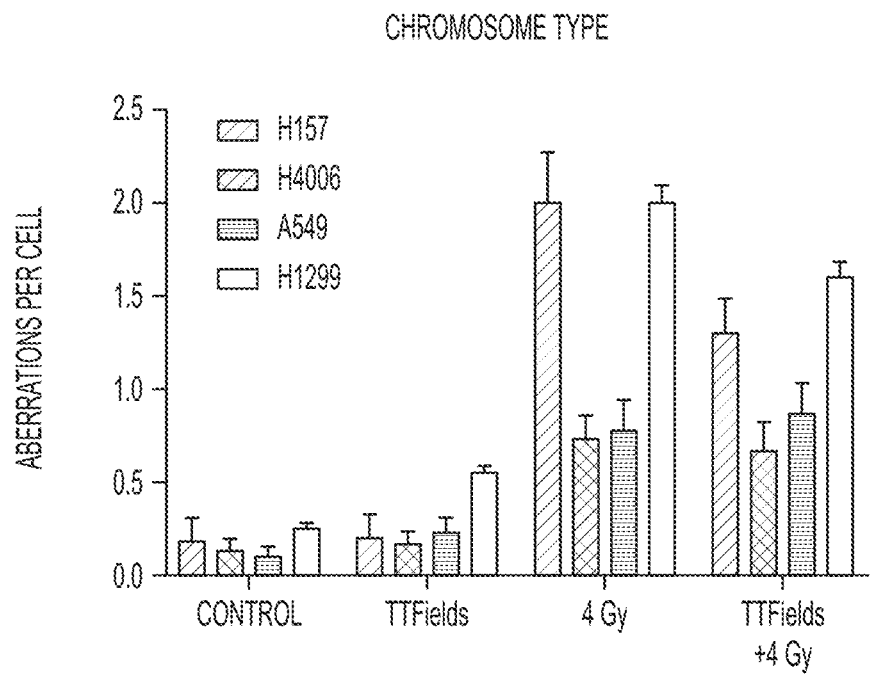
FIG. 5E shows the frequency of chromosome-type aberrations after TTFields exposure in combination with radiation.

To further confirm the effects of TTFields on DNA damage, the inventors performed cytogenetic analysis to validate the findings associated with DNA repair foci at 48 h post irradiation. TTFields alone significantly increased the frequency of chromatid-type but not chromosome-type aberrations in all cell lines examined, consistent with the finding that TTFields cause DNA damage. These findings are depicted in FIG. 5D, which shows that TTFields exposure for 48 h resulted in the induction of chromatid-type aberrations in the panel of NSCLC lines; and in FIG. 5 E, which shows the frequency of chromosome-type aberrations after a 48 h TTFields exposure in combination with radiation. Note that in FIGS. 5A-5E, the error bars represent the S.E.M. of three separate experiments and asterisks represent a significant difference (P<0.05) between indicated conditions. It appears that the combined effect of TTFields plus IR increased both chromatid-type and chromosome-type aberrations, albeit not at a higher frequency than that of each agent alone.

TTFields Sensitize NSCLC Cells to IR:

After observing the reduction in BRCA1 expression, a reduction in DNA DSB repair capacity, and increased chromatid damage with TTFields exposure, the radioresponse of the panel of NSCLC cell lines was determined via clonogenic cell survival after the cells received either 2 or 4 Gy IR followed by TTFields treatment for 24, 48, and 72 h. The results of the inventors' evaluation of radiosensitization effect of TTFields in combination with IR are provided in Table 2 and FIG. 6. For this experiment, TTFields treatment was applied alone or immediately following treatment with 2 or 4 Gy of 137Cs $\gamma$-rays. Survival was then assessed in all cell lines following 24, 48, or 72 h of TTFields induction. Radiosensitization of TTFields was evaluated by the Highest Single Agent approach for combinations of 2 Gy+TTFields and 4 Gy+TTFields. All of the cell lines displayed an enhanced sensitivity to IR, although, consistent with earlier results, the degree of sensitization varied between cell lines. Note that in FIG. 6, the error bars represent the S.E.M. of three separate experiments and asterisks represent values where survival was significantly decreased (P<0.05).

The inventors considered the combined effect of TTFields and IR to be synergistic if the combination index (CI) was >1 and the P-value was <0.05 for a given time point post IR and a given cell line (N=3) (see Materials and Methods). Based on these criteria, the combined effect of 4 Gy IR and TTFields on cell death was found to be synergistic in all the cell lines tested, whereas the combined effect of 2 Gy IR and TTFields on cell death was found to be synergistic in the H157, H4006, A549, and H1650 cell lines.

TABLE 2

| Cell line | Time point (h) | CI (TTFields + 2 Gy) | P-value | CI (TTFields + 4 Gy) | P-value |
|---|---|---|---|---|---|
| H157 | 24 | 1.48 | <0.0001 | 2.23 | 0.001 |
| H157 | 48 | 2.08 | <0.0001 | 1.14 | 0.003 |
| H157 | 72 | 1.15 | 0.048 | 1.18 | 0.01 |
| H4006 | 24 | 0.88 | 0.14 | 1.88 | 0.001 |
| H4006 | 48 | 1.01 | <0.0001 | 1.74 | 0.003 |
| H4006 | 72 | 0.58 | 0.004 | 1.01 | 0.05 |
| A549 | 24 | 1.88 | <0.0001 | 1.5 | 0.12 |
| A549 | 48 | 1.14 | 0.001 | 2.36 | <0.0001 |
| A549 | 72 | 0.86 | 0.14 | 1.99 | 0.0007 |
| H1650 | 24 | 1.48 | 0.17 | 1.19 | 0.64 |
| H1650 | 48 | 1.21 | <0.0001 | 0.9 | 0.21 |
| H1650 | 72 | 1.35 | <0.0001 | 1.47 | 0.03 |
| H1299 | 24 | 0.91 | 0.68 | 3.32 | <0.0001 |
| H1299 | 48 | 0.79 | 0.09 | 3.97 | <0.0001 |
| H1299 | 72 | 0.94 | 0.04 | 2.42 | 0.0003 |

Figure 7:
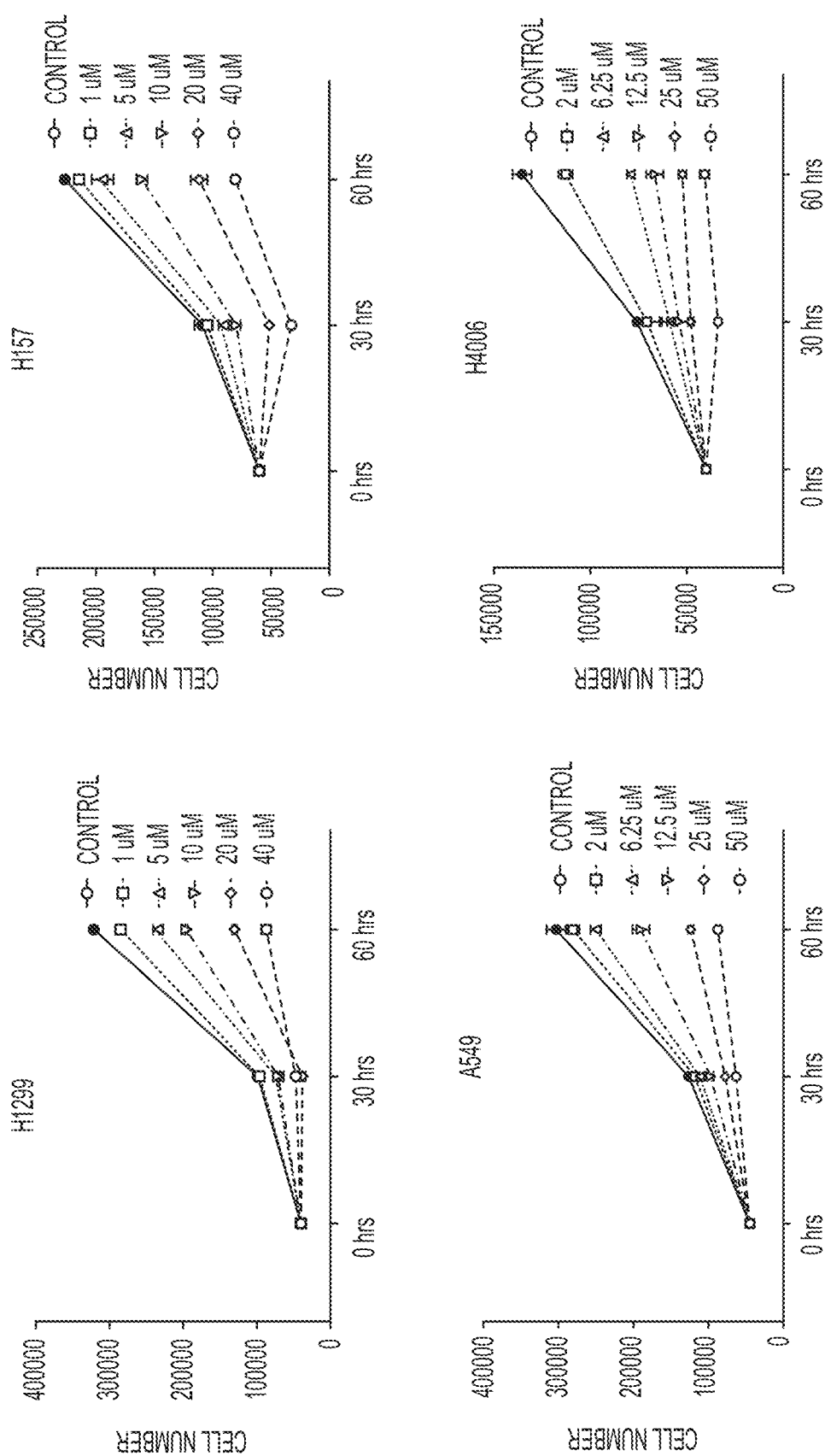
FIG. 7 depicts baseline growth curves for exposing various NSCLC cell lines to different concentrations of Olaparib without TTFields.
Figure 8:
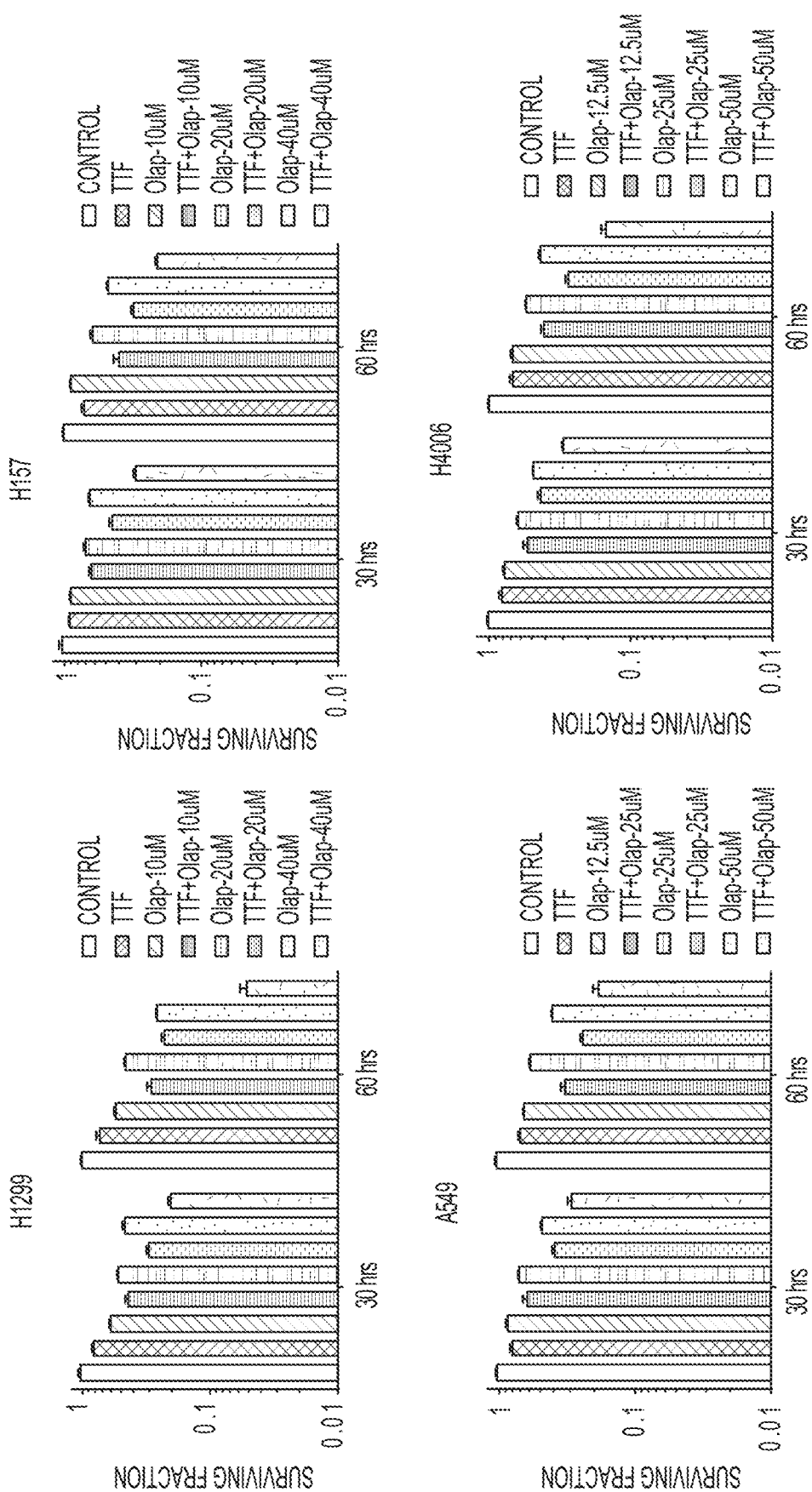
FIG. 8 depicts clonogenic assays showing the combination effect for different combinations of various concentrations of Olaparib and TTFields.

TTFields Synergistically Enhanced the Cytotoxicity of the PARP Inhibitor Olaparib:

Experiments similar to those discussed above in connection with Table 2 and FIG. 6 were also conducted, but with exposure to IR replaced with exposure to three different concentrations (either 10, 20, and 40 µM; or 12.5, 25, and 50 µM, depending on the cell line) of the PARP inhibitor Olaparib. More specifically, Olaparib at each of the different concentrations was added to cells and the cells were then exposed to TTFields for 30 or 60 h (or not exposed to TTFields for the control) and immediately plated for survival. Baseline growth curves for exposing the various NSCLC cell lines to different concentrations of Olaparib without TTFields are depicted in FIG. 7. The combination effect was evaluated using the Highest Single Agent approach for various combinations and are listed in Table 3. Clonogenic assays are depicted in FIG. 8 for the different combinations of drug concentration and TTFields exposure time in Table 3.

The inventors considered the combined effect of TTFields and Olaparib to be synergistic if the combination index (CI) was >1 and the P-value was <0.05 for a given time point and a given cell line. Based on these criteria and the data summarized in Table 3 below, the combined effect of TTFields and all tested concentrations of Olaparib on cell death was found to be synergistic in the H1299, H157, A549, and H4006 cell lines.

TABLE 3

| Cell line | Time point (h) | TTFields + Olap 10 µM | | TTFields + Olap 20 µM | | TTFields + Olap 40 µM | |
|---|---|---|---|---|---|---|---|
| | | CI | P-value | CI | P-value | CI | P-value |
| H1299 | 30 | 1.12 | 0.016 | 1.42 | 0.012 | 1.9 | 0.019 |
| H1299 | 60 | 1.4 | 0.024 | 1.5 | 0.019 | 3.7 | 0.010 |
| H157 | 30 | 1.3 | 0.018 | 1.44 | 0.022 | 1.78 | 0.016 |
| H157 | 60 | 1.63 | 0.022 | 1.43 | 0.023 | 1.68 | 0.020 |

| Cell line | Time point (h) | TTFields + Olap 12.5 µM | | TTFields + Olap 25 µM | | TTFields + Olap 50 µM | |
|---|---|---|---|---|---|---|---|
| | | CI | P-value | CI | P-value | CI | P-value |
| A549 | 30 | 1.12 | 0.031 | 1.46 | 0.021 | 1.32 | 0.015 |
| A549 | 60 | 1.39 | 0.013 | 1.716 | 0.013 | 1.53 | 0.008 |
| H4006 | 30 | 1.17 | 0.03 | 1.17 | 0.02 | 1.32 | 0.02 |
| H4006 | 60 | 1.13 | 0.02 | 1.34 | 0.02 | 1.96 | 0.01 |

The Triple Combination of TTFields, IR, and the PARP Inhibitor Olaparib Synergistically Enhances Cell Killing:

Experiments similar to those discussed above in connection with Table 2 and FIG. 6 were also conducted for H1299 and H157 cell lines, both with and without the PARP inhibitor Olaparib. More specifically, Olaparib (at a concentration of 20 µM) was added to cells, the cells were immediately exposed to TTFields for 24, 28, or 72 h, removed, irradiated (at different doses of radiation), and immediately plated for survival.

Figure 9A:
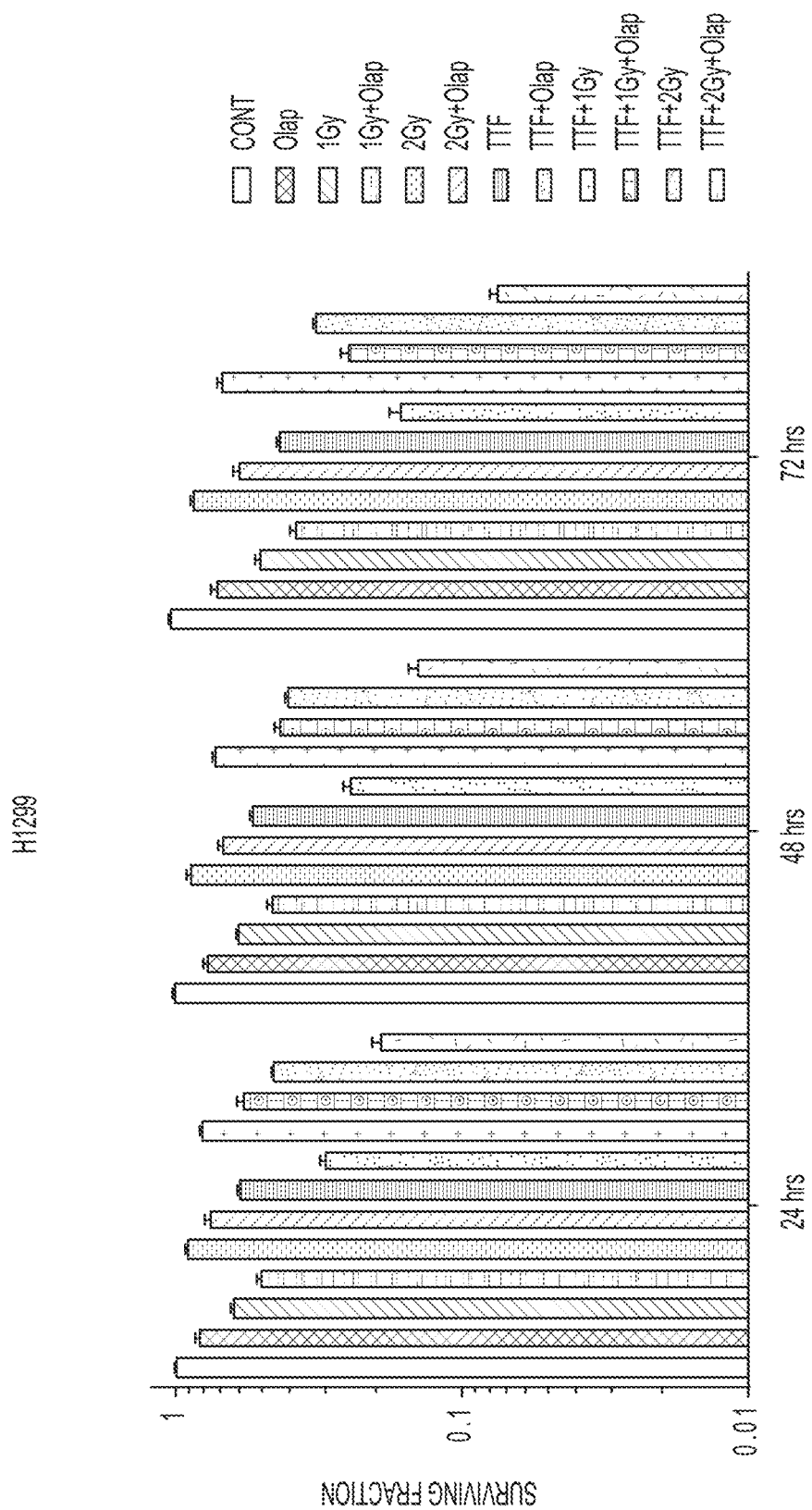
FIGS. 9A and 9B depict clonogenic assays showing the combination effect for different combinations of TTFields, RT dosage, and Olaparib for H1299 and H157 cell lines, respectively.
Figure 9B:
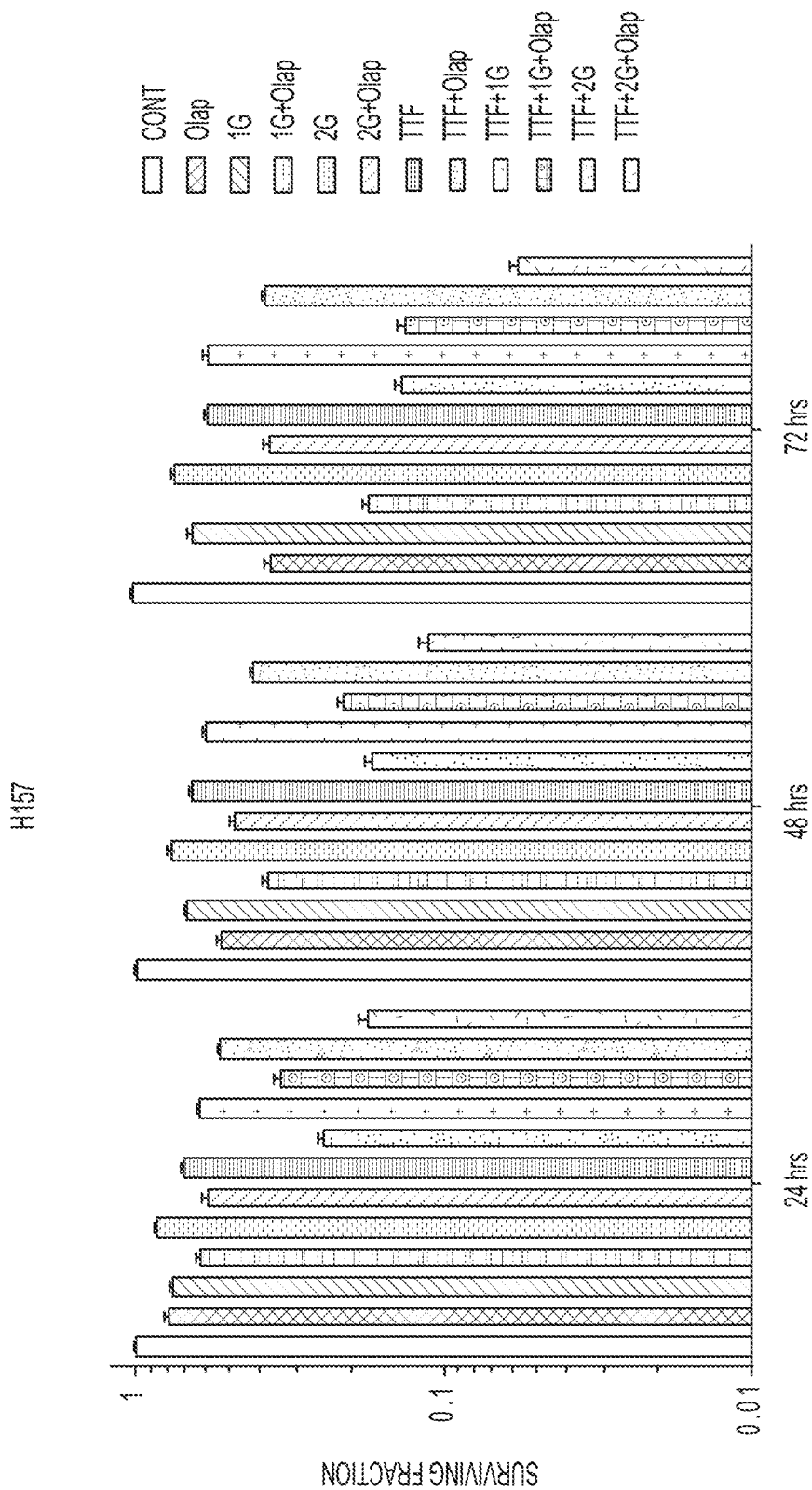

The combination effect was evaluated using the Highest Single Agent approach and are listed in Table 4 and depicted in FIGS. 9A and 9B, which summarize the clonogenic assays for the different combinations of RT dosage and TTFields exposure time in the table, both with and without the Olaparib.

The inventors considered the combined effect of TTFields and Olaparib to be synergistic if the combination index (CI) was >1 and the P-value was <0.05 for a given time point and a given cell line. Based on these criteria and the data summarized in Table 4 below, the combined effect of TTFields, IR, and Olaparib on cell death was found to be synergistic in the H1299 and H157 cell lines.

TABLE 4

| | TTFields + Olap | | TTFields + 1 Gy | | TTFields + 2 Gy | | TTFields + Olap + 1 Gy | | TTFields + Olap + 2 Gy | |
|---|---|---|---|---|---|---|---|---|---|---|
| Time | CI | P-value | CI | P-value | CI | P-value | CI | P-value | CI | P-value |
| H1299 | | | | | | | | | | |
| 24 h | 1.03 | 0.019 | 0.99 | 0.024 | 1.15 | 0.021 | 1.64 | 0.016 | 1.96 | 0.011 |
| 48 h | 1.02 | 0.015 | 1.00 | 0.03 | 1.30 | 0.020 | 1.70 | 0.014 | 2.20 | 0.011 |
| 72 h | 1.06 | 0.022 | 1.03 | 0.03 | 1.98 | 0.029 | 1.89 | 0.015 | 3.08 | 0.011 |
| H157 | | | | | | | | | | |
| 24 h | 0.97 | 0.022 | 1.14 | 0.023 | 1.45 | 0.020 | 2.25 | 0.019 | 2.36 | 0.016 |
| 48 h | 1.02 | 0.014 | 0.90 | 0.015 | 1.55 | 0.015 | 2.12 | 0.015 | 2.07 | 0.008 |
| 72 h | 1.49 | 0.016 | 0.92 | 0.019 | 1.74 | 0.016 | 1.66 | 0.015 | 2.57 | 0.010 |

DISCUSSION

The inventors confirmed that TTFields have antiproliferative effects, induce cell death, and alter the distribution of cells through the cell cycle, resulting in an enrichment of G2/M populations and the generation of a sub-G1 population indicative of apoptotic cells.

Earlier, Gera et al. showed that TTFields' sensitivity is dependent on p53 status in colon cancer cells; however, cell proliferation and survival results from the inventors' study and studies by others suggest that TTFields' effects are independent of p53 status (Table 1 and FIG. 1). Because the presence of a sub-G1 population and the increase in G2/M cells are likely not sufficient to account for the differences in survival observed when TTFields were applied across the NSCLC cell panel, the inventors postulated that there are other novel mechanism(s) by which TTFields lead to cell killing. The inventors divided the NSCLC cell lines into two categories, that is, more responsive cell lines (H157 and H4006) and less responsive (A549, H1299, and H1650) cell lines, and conducted gene expression analysis to understand the basis for the differential response of NSCLC cell lines to TTFields.

The molecular basis of the differential responses to TTFields was demonstrated by supervised clustering analysis that clearly segregated the cell lines into a more responsive cluster and a less responsive cluster. To further elucidate the differences, the inventors compared signaling pathways involved in the genes that responded to TTFields in each of the two cell line groups. The majority of the pathways were common in more responsive (15 out of 19 associated pathways) and less responsive cell lines (15 out of 27 associated pathways), which are related to cell cycle and DNA-damage response pathways. While these pathways have been reported in previous studies, downregulation of the BRCA1 signaling pathway with TTFields exposure is a novel finding. The fact that BRCA1 pathway downregulation is more pronounced in the more responsive cell lines than in the less responsive cell lines, evident by the negative z-scores (FIG. 3A), suggests an inverted correlation between BRCA1 pathway activity and the sensitivity of cellular response to TTFields.

BRCA1 together with BRCA2 have an important role in maintaining replication fidelity through the repair of DSB damage by mediating homologous recombination and through non-homologous end joining during S and G2 phases of cell cycle. DSBs can occur during IR exposure or as by-products of DNA replication. BRCA1 mutant mice exhibit chromosome translocation and chromatid aberrations, and BRCA2 mutant mice accumulate chromatid breaks and aberrant chromatid exchanges. BRCA1 defects have been previously identified in multiple cancers including breast and pancreas. Defects in the BRCA genes predispose cells to therapeutics targeting single-strand break (SSB) repair pathways, such as PARP inhibitors, resulting in what has been coined 'synthetic lethality.'

On the basis of the inventors' findings, the inventors propose that TTFields exposure may induce a conditional vulnerability, that is, they induce BRCAness because of the downregulation of the BRCA1 pathway genes. If this proposal is accurate, then TTFields could be applied in combination with PARP inhibitors without the potential for developing therapy-resistant recurrent tumors as is common with molecularly targeted therapies. This is supported by the inventors' results showing the gradual accumulation of γ-H2AX foci following TTFields application over time and slowed DNA repair kinetics following IR exposure (γ-H2AX foci and colocalized γ-H2AX and 53BP1 foci (FIGS. 5A-C). Indeed, the more responsive cell lines had, on average, more residual DNA repair foci at 24 and 48 h post-IR than the less responsive cell lines, and Kim et al. also showed accumulation of γ-H2AX upon TTFields treatment. 53BP1 localizes to DNA DSBs, which are physically distinct from DNA replication stress, whereas γ-H2AX recruits MRE11, KU70, KU80 and RAD51 to stalled replication forks at early time points. While not being bound by this theory, the inventors believe that TTFields not only slow down DNA damage repair kinetics but also induce replication stress based upon the significant differences seen in colocalized γ-H2AX/53BP1 foci (FIGS. 5A and 5C) and γ-H2AX foci alone (FIGS. 5B and C). Furthermore, the increased frequency of chromatid-type aberrations (FIGS. 5D and 5E) is consistent with ongoing replicative stress induced by TTFields because a defective response to replication stress leads to an accumulation of chromatid-type aberrations. Hence, the inventors postulate that TTFields induce replication stress and the reduction of BRCA1 pathway proteins leads to an increased frequency of chromatid-type aberrations. The notion that TTFields induces DNA replication stress can explain both the increase in DNA damage foci and the elevated frequency of chromatid-type aberrations. Ongoing studies by the inventors' group are seeking to better understand the molecular underpinning of this induced replication stress.

Figure 6:
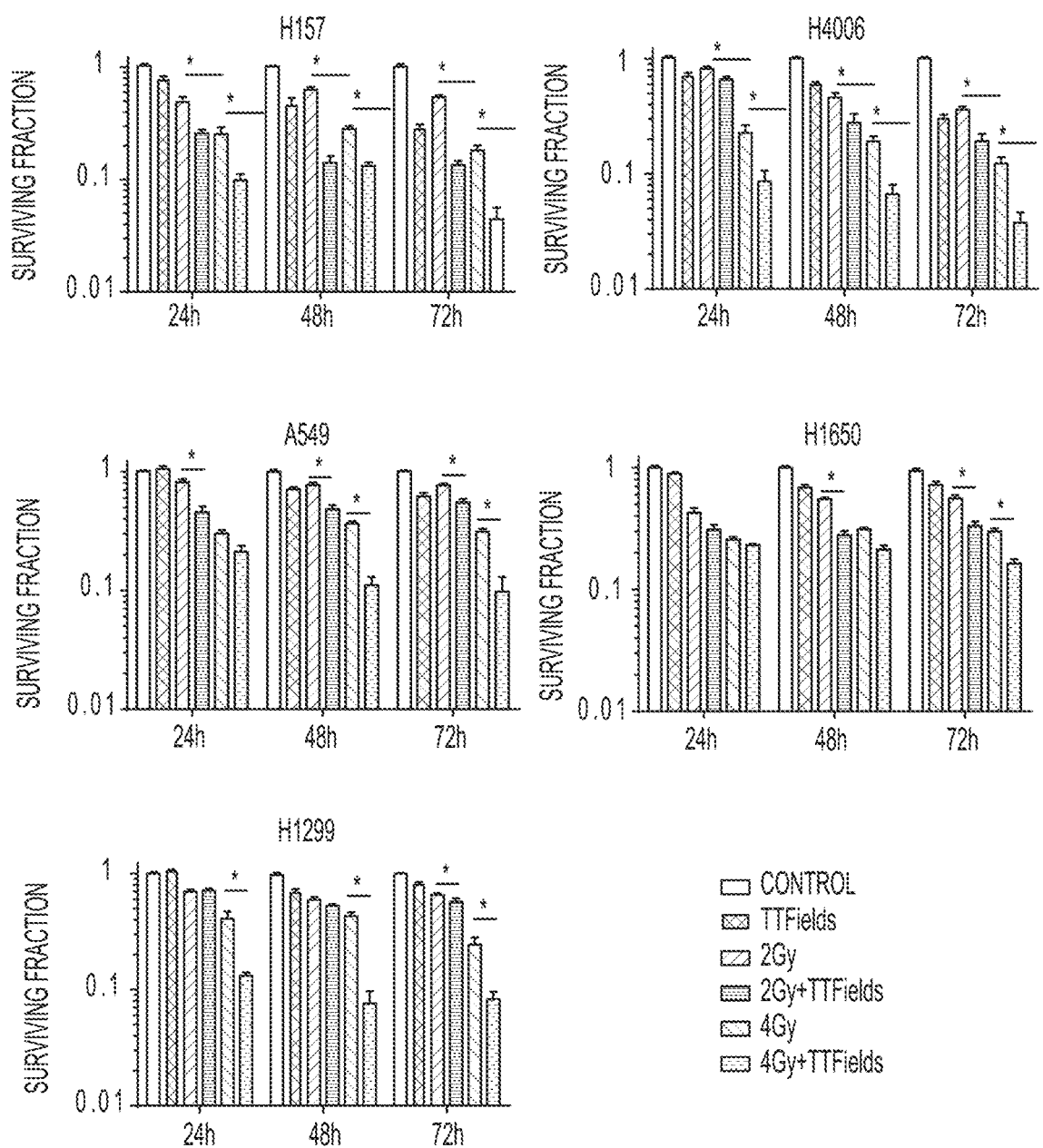
FIG. 6 depicts an evaluation of the radiosensitization effect of TTFields in combination with IR.

The reduced DNA DSB repair capacity seen in all cell lines when TTFields were applied post-IR is clearly linked to reduced cell survival (FIG. 6 and Table 2). These data are consistent with findings reported by Kim et al. in which TTFields sensitized GBM cell lines to IR. In contrast to the inventors' methods, these authors applied TTFields prior to irradiation, whereas the inventors first irradiated the cells and then immediately applied TTFields assuming that the chromosomal damage generated by IR would enhance the disruption of mitosis caused by TTFields exposure. Interestingly, both prior and post-TTFields treatment sensitize cells to IR, which could have an impact on treatment sequencing.

Turning next to the data discussed above in connection with FIGS. 7-9 and Tables 3 and 4, it appears that TTFields downregulate the FANC/BRCA pathways which are crucial for homologous recombination repair and which results in DNA replication fork stalling. PARP-1 is then hyperactivated to reactivate stalled replication forks. PARP inhibitors block this replication fork re-activation. Furthermore, by downregulating BRCA2 via TTFields and inhibition of PARP-1 activity, stalled replication fork DNA is no longer protected from Mre-11 degradation. By causing replication stress and the downregulation of key genes associated with DNA repair and DNA replication fork protection or restart, TTFields generate a synergistic vulnerability to agents like PARP inhibitors.

Figure 10:
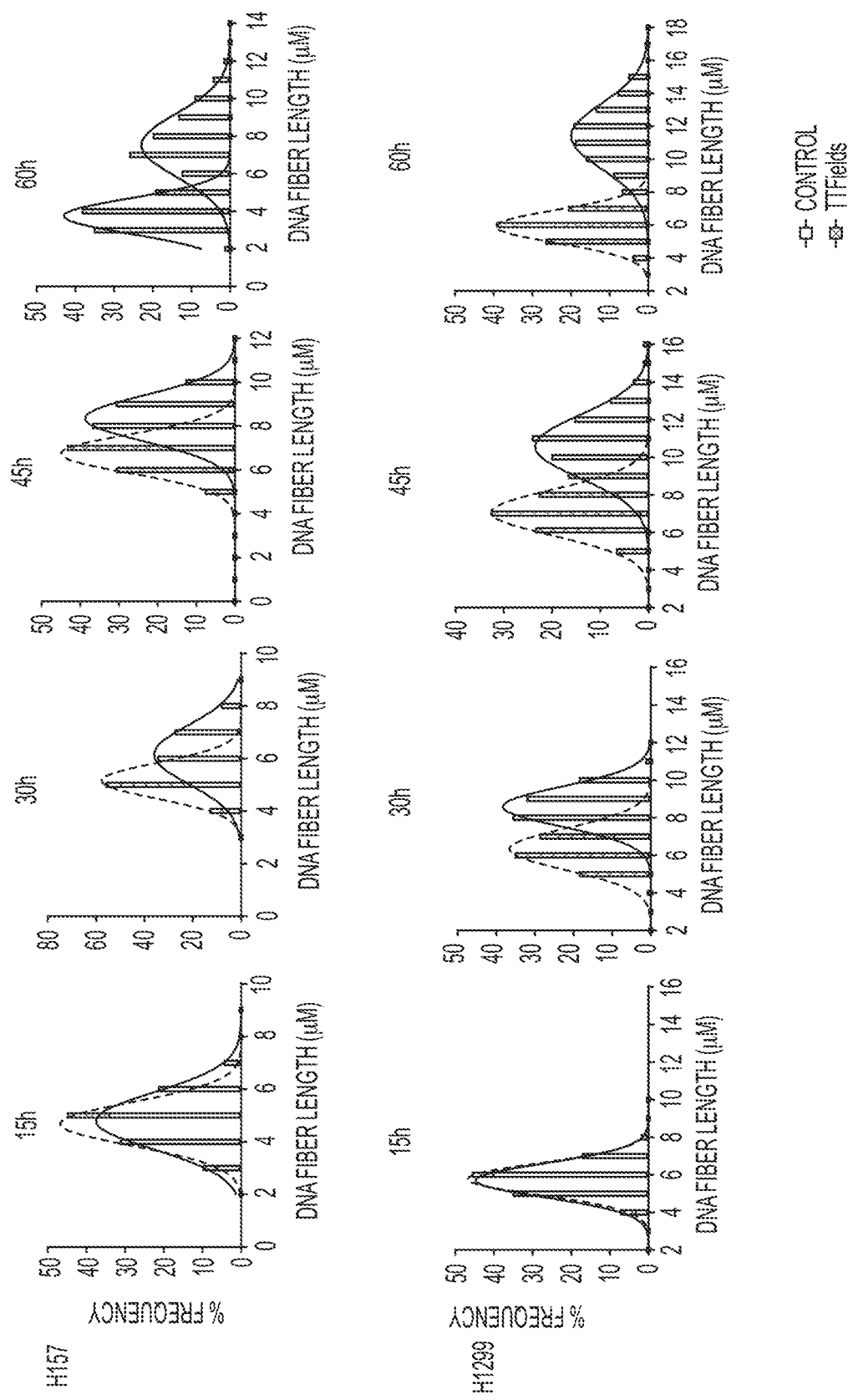
FIG. 10 depicts data showing that TTFields inhibit the increase in length of newly replicated DNA fibers.

The inhibition of DNA replication fork growth is supported by the data depicted in FIG. 10, which shows that TTFields inhibit the increase in length of newly replicated DNA fibers. More specifically, this data shows that there is no increase in newly replicated DNA when cells are exposed to TTFields for up to 60 h as measured by the DNA fiber assay using halogenated nucleotides analogues in both H157 and H1299 cells.

Figure 11:
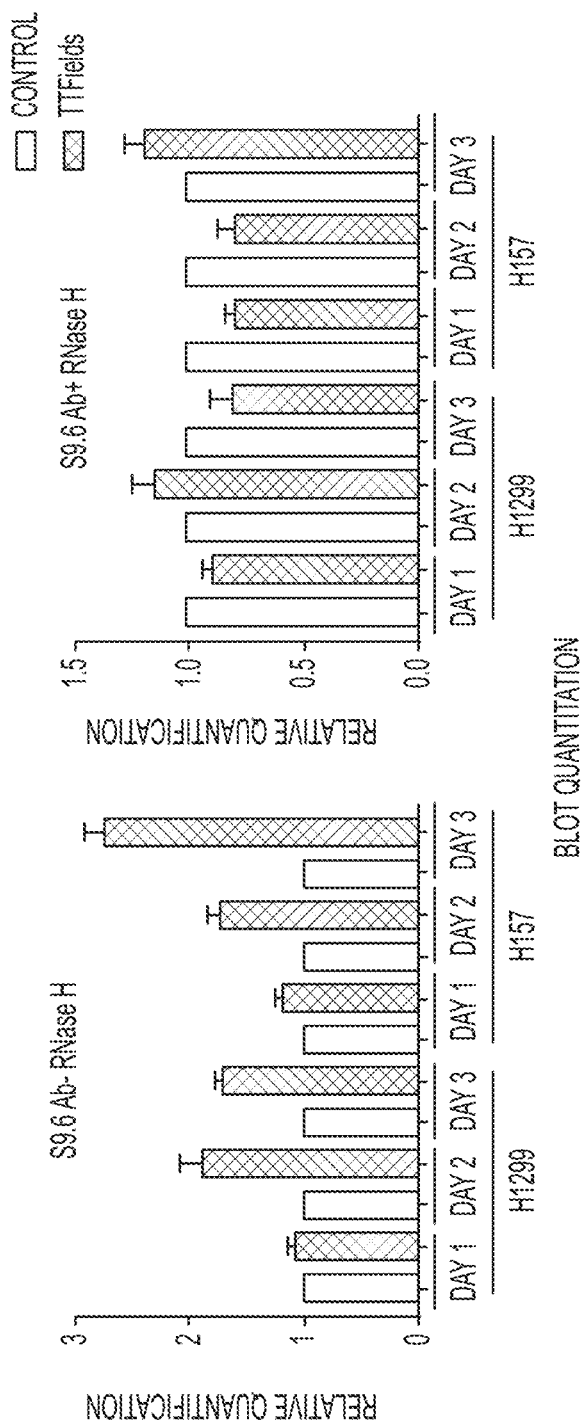
FIG. 11 shows that TTFields cause replication fork stress which results in R loop formation.

Further support appears in FIG. 11, which shows that TTFields cause replication fork stress which results in R loop formation. More specifically, R-loops formed by TTFields exposure were quantified by dot-blot using a DNA-RNA hybrid specific S9.6 antibody in H157 and H1299 cells. R loops, which are DNA:RNA hybrids are markers of DNA replication fork stress and collapse that end in mitotic catastrophe. And FIG. 11 shows that exposure of H157 and H1299 to TTFields increases R-loop formation.

In conclusion, TTFields induce a global antiproliferative and cytotoxic effect on dividing cell populations; however, the relative sensitivity of cells to TTFields varies. These antitumor properties are due to multiple mechanisms, likely acting in concert, that would suggest TTFields should be utilized as an adjuvant modality with RT and/or PARP inhibitors. Indeed, the inventors' data suggest by gaining additional insight into understanding the underlying molecular mechanisms governing TTFields' antitumor effects optimizing combinatorial strategies of TTFields, IR and/or PARP inhibitors in preclinical models is appropriate. At this junction PARP inhibitors are particularly attractive, based on the data set forth herein. Lastly, whether specific molecular signatures as reported in this study will predict which patients will respond better to TTFields is worth exploring clinically where possible.

Materials and Methods

Cell Culture:

Human NSCLC cell lines (H157, H4006, A549, H1299 and H1650) were purchased from American Tissue Culture Collection. All these cell lines were grown in RPMI medium supplemented with 10% (v/v) fetal bovine serum (Atlanta Biologicals, Flowery Branch, Ga., USA) and penicillin/streptavidin (final concentration 50 μg/ml; Sigma-Aldrich, St. Louis, Mo., U29SA). All cells were grown at 37° C. in a humidified incubator constantly supplied with 5% $CO_2$.

Tumor Treating Fields:

The inventors used the inovitro system (NovoCure Ltd, Haifa, Israel) to generate TTFields that use two pairs of electrodes printed perpendicularly on the outer walls of a Petri dish composed of high dielectric constant ceramic (lead magnesium niobate-lead titanite (PMN-PT)). The transducer arrays were connected to a sinusoidal waveform generator that generate low-intensity electric fields at the desired frequencies in the medium as summarized in Table 1 above. The orientation of the TTFields was switched 90° every 1 s, thus covering the majority of the orientation axis of cell divisions, as previously described by Kirson et al. Plate temperature was maintained at 37° C. by placing the plates in a refrigerated incubator where the temperature was maintained at 19° C. to dissipate the heat generated by the inovitro system. The temperature was measured by 2 thermistors (Omega Engineering, Stamford, Conn., USA) attached to the ceramic walls. All cell suspensions were grown on a cover slip inside the inovitro dish (NovoCure Ltd) and treated with TTFields for the times indicated in the figure legends.

Cell Growth Assay:

Human NSCLC (H157, H4006, A549, H1299 and H1650) cell lines were treated with different frequencies of TTFields indicated for 24, 48 and 72 h, and cell growth was counted using a Beckman coulter counter (Beckman Coulter Inc, Indianapolis, Ind., USA) in triplicates for each sample. Growth curve graphs were drawn using the average cell number counted at each time point and the given TTFields frequency using GraphPad Prism V.6 (GraphPad Software Inc, La Jolla, Calif., USA).

Cell Cycle Analysis:

Cells at specific times and treatments were harvested and fixed in 75% ice-cold ethanol at −20° C. for 24 h. Fixed cells were washed with PBS and incubated in 500 µl of PI staining solution, that is, PBS containing 1 mg/ml RNAse A (Sigma-Aldrich), 0.05% triton X-100 and 30 µg/ml of PI (Sigma-Aldrich) for 30 min at 37° C. The cell cycle distribution was determined using a FACSCalibur system (BD Biosciences, San Jose, Calif., USA). More than 10,000 cells per sample were counted and the results were analyzed using FlowJo software v8.7.1 (Tree Star Inc, Ashland, Oreg., USA).

Labeling and Hybridization of RNA for Gene Expression Analysis:

Illumina Whole Genome HumanWG6 v4 Expression BeadChips (Illumina Inc, San Diego, Calif., USA) were used. Each RNA sample (0.5 µg) was amplified using the Illumina TotalPrep RNA amplification kit with biotin UTP (Enzo Life Sciences, Inc., Farmingdale, N.Y., USA) labeling. T7 oligo(dT) primers were used to generate single-stranded cDNA followed by a second-strand synthesis to generate double-stranded cDNA, which is then column-purified. In vitro transcription was done to synthesize biotin-labeled cRNA using T7 RNA polymerase. The cRNA was then column-purified and checked for size and yield using the Bio-Rad Experion system (Bio-Rad Laboratories, Hercules, Calif., USA). cRNA (1.5 µg) was then hybridized for each array using standard Illumina protocols with streptavidin-Cy3 (Amersham Biosciences, Piscataway, N.J., USA) being used for detection. Slides were scanned on an Illumina Beadstation (Illumina Inc).

Data Processing and Significance Analysis of Differential Gene Expression:

Summarized expression values for each probe set were generated using BeadStudio 3.1 (Illumina Inc). The data were background-subtracted and quantile-quantile-normalized across samples using the MBCB algorithm. Normalized gene expression values were used to generate plots for comparisons. Analysis of differentially expressed genes in treated cell lines was performed using SAM. FDR<0.05 was considered to be statistically significant. Clustering analysis and heatmaps were generated using the Partek Genomic Suite software (Partek Incorporated, St. Louis, Mo., USA). Gene ontology and pathway analysis was performed using IPA (QIAGEN, Redwood City, Calif., USA).

Immunoblotting:

Laemmli sample buffer (4×; Bio-Rad Laboratories) was added to 30 µg of each protein sample and the mixtures were boiled at 95° C. for 10 min. Protein mixtures were then loaded on 10% SDS-PAGE gel followed by transfer to PVDF membrane for 1 h at 90 V at 4° C. The membrane was blocked with 5% fat-free milk in PBST for 1 h at room temperature and probed with anti (3-actin (1:5000; Cell Signaling, Danvers, Mass., USA), anti-BRCA1 (1:1000), anti-FANCD2 (1:2000) and anti-FANCA (1:500; Novus Biologicals LLC, Littleton, Colo., USA) in PBST containing 2% bovine serum albumin (Thermo Fisher Scientific Inc, Bridgewater, N.J., USA) overnight at 4° C. Membranes were washed with phosphate-buffered saline with 0.1% Tween-20 (PBST; 3×10 min, each) followed by incubation with secondary antibodies (1:5000) conjugated with horseradish peroxidase (GE Healthcare, Buckinghamshire, UK) for 1 h at room temperature. Membranes were developed using a chemiluminescence detection kit (Thermo Scientific, Rockford, Ill., USA) on FluorChem M system (ProteinSimple, San Jose, Calif., USA). Quantification was done using the ImageJ software (NIH, Bethesda, Md., USA) and normalized using the corresponding actin density.

Immunofluorescence:

Cells were seeded on glass coverslips and after treatment cells were washed and fixed with ice-cold methanol. The samples were blocked with 10% normal goat serum for 1 h and incubated with phospho-histone-γ-H2AX antibody (Ser139; Upstate Biotechnology, Temecula, Calif., USA) and p53-binding protein 1 (53BP1) antibody (Cell Signaling). Samples were washed three times for 5 min in PBS, and then incubated with Alexa Fluor 488-conjugated anti-rabbit antibody and Alexa Fluor 555-conjugated anti-mouse antibody (Invitrogen, Carlsbad, Calif., USA) for 1 h. Nuclei were counterstained with DAPI contained in Vecatshield mounting medium (Vector Laboratories Inc, Burlingame, Calif., USA). The stained cells were then analyzed under a fluorescence microscope (Axio Imager M2, Carl Zeiss, Thornwood, N.Y., USA) with a ×63 objective (oil immersion, aperture 1.3) with five slices of z-stacks of $0.2\mu_M$ thickness each. Quantitative image analysis of 40 nuclei from each experiment was performed using Cell module in Imaris software version 8.0 (Bitplane, Concord, Mass., USA).

Cytogenetic Analyses:

Preparation of metaphase chromosome spreads and cytogenetic analysis were performed. Briefly, cultured cells were treated with 1 µM colcemid solution (Thermo Scientific) for 3-4 h at 37° C., trypsinized, incubated for 30 min in a hypotonic solution of 75 mM KCl solution and subsequently fixed with 3:1 methanol to acetic acid. Samples were then dropped on to glass slides and stained with either 5% Giemsa (Sigma-Aldrich) or prolong antifade gold reagent with DAPI (Life Technologies, Carlsbad, Calif., USA) for scoring. The presence of chromosome-type aberrations (deletions, dicentric chromosomes and rings) and chromatid-type (gaps, breaks, deletions, and radial chromosome arrangements) was detected under a microscope (Axio Imager M2, Carl Zeiss) and −30 metaphase cells per treatment group were scored and averages displayed as the frequency of aberrations per cell.

Radiation Exposure and Clonogenic Cell Survival:

To study the effect of radiation sensitivity on NSCLC cells, exponentially growing cells were treated with IR using a Mark II Cs irradiator (J L Shepherd and Associates) at a dose rate of 3.47 Gy/min, followed by immediate application of TTFields for 24, 48 and 72 h. Cells were then re-seeded into 60 mm dishes and incubated for up to 2 weeks. Colonies containing 50 or more cells were considered viable. The data are presented as the mean±S.E.M. of three independent experiments. The radiosensitization effect of TTFields was evaluated according to The Highest Single Agent approach by calculating the CI as given below.

$$CI = SF_{IR} \times SF_{TTFields}/SF_{IR+TTFields}$$

Where SF=Survivalfraction

The combination effect was considered enhanced/synergistic when CI>1, additive when CI=1. Statistical significance for a positive effect was determined by the P-value of a two-way ANOVA multiple comparison statistical test comparing the combination (TTFields plus IR) to the single agent showing the greatest cell killing for a given dose and time after IR.

For the Triple Combination of TTFields, IR, and Olaparib, CI was calculated using the following equations:

$$CI(TTFields+olap) = (SF_{Olap} \times SF_{TTFields})/SF_{Olap+TTFields}$$

$$CI(TTFields+1Gy) = (SF_{1Gy} \times SF_{TTFields})/SF_{1Gy+TTFields}$$

$$CI(TTFields+2Gy) = (SF_{2Gy} \times SF_{TTFields})/SF_{2Gy+TTFields}$$

$$CI(TTFields+olap+1Gy) = (SF_{1Gy+Olap} \times SF_{TTFields})/SF_{Olap+TTFields+1Gy}$$

$$CI(TTFields+olap+2Gy) = (SF_{2Gy+Olap} \times SF_{TTFields})/SF_{Olap+TTFields+2Gy}$$

Where SF=Survival fraction

CONCLUSION

The in vitro experiments described above demonstrate that applying TTFields in combination with a PARP inhibitor provides a synergistic effect against NSCLC cells; and that TTFields in combination with both IR and a PARP inhibitor also provides a synergistic effect against NSCLC cells.

Note that although the examples discussed herein uses Olaparib in combination with TTFields, in alternative embodiments other PARP inhibitors (including but not limited to Rucaparib and Niraparib) may be used in place of Olaparib. Note also that while the experimental results described herein were obtained in vitro, the inventors expect that they will carry over to the in vivo context.

These results establish that cancer cells can be killed by delivering a PARP inhibitor to the cancer cells and applying an alternating electric field with a frequency between 80 and 300 kHz to the cancer cells. At least a portion of the applying step is performed simultaneously with at least a portion of the delivering step. Note that in the in vitro context, the delivery of the PARP inhibitor to the cancer cells occurs continuously from a first time ($t_1$) when the PARP inhibitor is introduced into the container that is holding the cancer cells until such time ($t_2$) as the PARP inhibitor is removed or exhausted. As a result, if TTFields are applied to the cancer cells between $t_1$ and $t_2$, the applying step will be simultaneous with at least a portion of the delivering step. In the in vivo context, the delivery of the PARP inhibitor to the cancer cells occurs continuously from a first time ($t_1$) when the PARP inhibitor is circulating in the patient's body (e.g., after administering it systemically) or introduced into the vicinity of the cancer cells until such time ($t_2$) as the PARP inhibitor is eliminated from the patient's body or exhausted. As a result, if TTFields are applied to the cancer cells between $t_1$ and $t_2$, the applying step will be simultaneous with at least a portion of the delivering step.

Examples of PARP inhibitors that may be used for the methods described herein include Olaparib, Rucaparib, and Niraparib. The optimal frequency and field strength will depend on the particular type of cancer cell being treated. For certain cancers, the optimum frequency will be between 100 and 200 kHz and the field strength will be at least 1 V/cm. In some embodiments, a deviation from the optimum frequencies may be made. For example, when the optimum frequency for treatment is 100 kHz, frequencies down to 80 kHz may still be effective. Or when the optimum frequency for treatment is 200 kHz, frequencies up to 300 kHz may still be effective.

In those embodiments that include radiation treatment, the radiation treatment may be performed before the applying step has begun, after the applying step has ended, or while the applying step is ongoing.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof

What is claimed is:

1. A method of killing lung cancer cells, the method comprising:
   delivering a PARP inhibitor to the lung cancer cells; and
   applying an alternating electric field to the lung cancer cells, the alternating electric field having a frequency between 80 and 300 kHz, wherein at least a portion of the applying step is performed simultaneously with at least a portion of the delivering step.

2. The method of claim 1, wherein the PARP inhibitor comprises Olaparib.

3. The method of claim 1, wherein the lung cancer cells are non-small cell lung cancer (NSCLC) cells.

4. The method of claim 1, wherein the applying step has a duration of at least 72 hours.

5. The method of claim 1, wherein the frequency of the alternating electric field is between 100 and 200 kHz.

6. The method of claim 1, wherein the alternating electric field has a field strength of at least 1 V/cm in at least some of the lung cancer cells.

7. The method of claim 6, wherein the applying step has a duration of at least 72 hours and wherein the frequency of the alternating electric field is between 100 and 200 kHz.

8. The method of claim 7, wherein the PARP inhibitor comprises Olaparib.

9. The method of claim 8, wherein the lung cancer cells are NSCLC cells.

10. The method of claim 1, wherein the concentration of the PARP inhibitor is from about 10 to about 50 μM.

11. The method of claim 10, wherein the PARP inhibitor is Olaparib.

12. A method of killing lung cancer cells, the method comprising:
    delivering a PARP inhibitor to the lung cancer cells;
    applying an alternating electric field to the lung cancer cells, the alternating electric field having a frequency between 80 and 300 kHz, wherein at least a portion of the applying step is performed simultaneously with at least a portion of the delivering step; and treating the lung cancer cells with a radiation therapy.

13. The method of claim 12, wherein the PARP inhibitor comprises Olaparib.

14. The method of claim 12, wherein the lung cancer cells are NSCLC cells.

15. The method of claim 12, wherein the alternating electric field has a field strength of at least 1 V/cm in at least some of the lung cancer cells.

16. The method of claim 15, further comprising repeating the delivering, applying, and treating steps at least five times.

17. The method of claim 16, wherein each repetition of the treating step comprises delivering at least 2 Gy of radiation to a target area.

18. The method of claim 16, wherein each repetition of the treating step comprises delivering at least 4 Gy of radiation to a target area.

19. The method of claim 16, wherein the frequency of the alternating electric field is between 100 and 200 kHz.

20. The method of claim 16, wherein the treating step is performed immediately after the applying step in each repetition.

21. The method of claim 16, wherein the applying step is performed immediately after the treating step in each repetition.

22. The method of claim 12, wherein the concentration of the PARP inhibitor is from about 10 to about 50 µM.

23. The method of claim 22, wherein the PARP inhibitor is Olaparib.

\* \* \* \* \*